US012669508B2

(12) United States Patent
Kleinberg et al.

(10) Patent No.: US 12,669,508 B2
(45) Date of Patent: Jun. 30, 2026

(54) METHODS TO PREVENT DISULFIDE SCRAMBLING FOR MS-BASED PROTEOMICS

(71) Applicant: Regeneron Pharmaceuticals, Inc., Tarrytown, NY (US)

(72) Inventors: Andrew Kleinberg, Roslyn Heights, NY (US); Yuan Mao, Hartsdale, NY (US); Ning Li, New Canaan, CT (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 916 days.

(21) Appl. No.: 17/976,330

(22) Filed: Oct. 28, 2022

(65) Prior Publication Data

US 2023/0243841 A1     Aug. 3, 2023

Related U.S. Application Data

(60) Provisional application No. 63/274,256, filed on Nov. 1, 2021.

(51) Int. Cl.
*G01N 33/68*          (2006.01)
(52) U.S. Cl.
CPC ..... *G01N 33/6848* (2013.01); *G01N 2560/00* (2013.01)
(58) Field of Classification Search
CPC ........... G01N 33/6848; G01N 2560/00; G01N 2440/12; G01N 2240/20; C07K 2317/40
See application file for complete search history.

(56) References Cited

U.S. PATENT DOCUMENTS

2011/0151493 A1     6/2011   Cockrill

OTHER PUBLICATIONS

Kellett-Clarke, CD44 Binding to Hyaluronic Acid is Redox Regulated by a Labile Disulfide Bond in the Hyaluronic Acid Binding Site, PLOS ONE, Sep. 17, 2015, pp. 1-18. (Year: 2015).*
Anastasia Albert et al: "General Approach To Determine Disulfide Connectivity in Cysteine-Rich Peptides by Sequential Alkylation on Solid Phase and Mass Spectrometry", Analytical Chemistry, vol. 88, No. 19, Sep. 22, 2016 (Sep. 22, 2016), pp. 9539-9546.
Cheng Ying et al: "Domain-specific free thiol variant characterization of an IgG1 by reversed-phase high-performance liquid chromatography mass spectrometry", Analytical Biochemistry, Academic Press, Amsterdam, NL, vol. 519, Dec. 7, 2016 (Dec. 7, 2016), pp. 8-14.
Anna C. Robotham et al: "Detection and quantification of free sulfhydryls in monoclonal antibodies using maleimide labeling and mass spectrometry", MABS, vol. 11, No. 4, Apr. 16, 2019 (Apr. 16, 2019), pp. 757-766.

(Continued)

*Primary Examiner* — Kathryn Elizabeth Limbaugh
(74) *Attorney, Agent, or Firm* — BakerHostetler

(57)          ABSTRACT

The present invention generally pertains to methods of preventing disulfide scrambling in non-reducing liquid chromatography-mass spectrometry analysis of a protein of interest. In particular, the present invention pertains to the addition of maleimide to a non-reducing liquid chromatography-mass spectrometry analysis of a protein to prevent disulfide scrambling.

20 Claims, 15 Drawing Sheets

Specification includes a Sequence Listing.

(56) References Cited

OTHER PUBLICATIONS

Trina Formolo et al: "Determination of the NISTmAb Primary Structure" In: "Chemistry, Process Design, and Safety for the Nitration Industry /ACS /Symposium Series", Oct. 15, 2015 (Oct. 15, 2015), American Chemical Society/Oxford University Press, US, XP055595854, ISSN: 0097-6156 vol. 1201, pp. 1-62.
International Search Report and Written Opinion mailed on Feb. 22, 2023 for International Application No. PCT/US2022/048242.

* cited by examiner

Maleamide

N-Hydroxy Maleimide

Maleimide

NEM
(N-Ethyl Maleimide)

■ STSESTAALGCLVK
■ TYTCNVDHKPSNTK
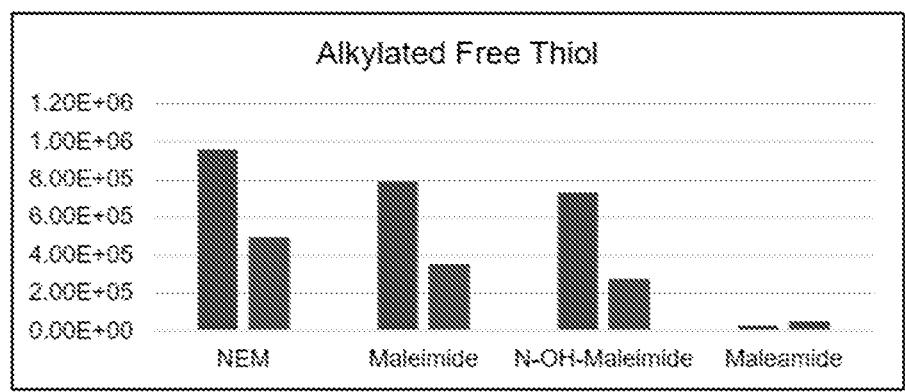
FIG. 6B
■ STSESTAALGCLVK
■ TYTCNVDHKPSNTK
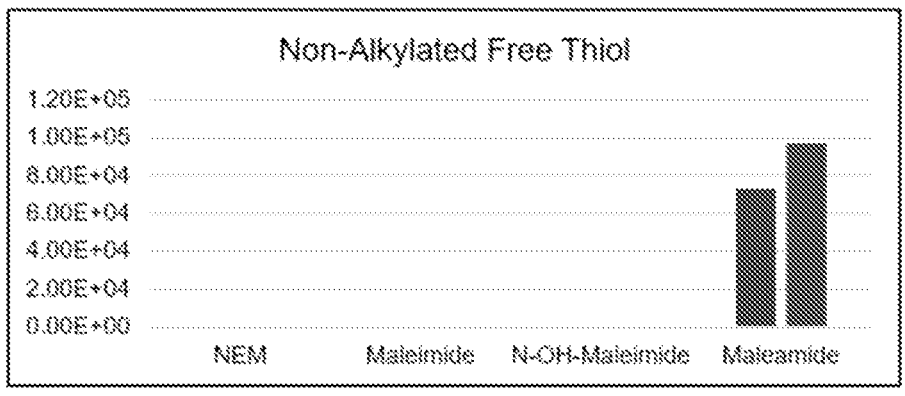

▓ STSESTAALGCLVK
▓ TYTCNVDHKPSNTK

▓ STSESTAALGCLVK
▓ TYTCNVDHKPSNTK

*1 Peptide at 52.0 min + maleimide: NQVSLTCLVK—W(maleimide)QQGNVFSCSVMHEALHNHYTQK*

*2 Peptide at 55.5 min + maleimide: G(maleimide)LEWVSGISWNSGR*

*3 Peptide at 69.8 min + maleimide: T(maleimide)HTCPPCPAPELLGGPSVFLFPPKPK—THTCPPCPAPELLGGPSVFLFPPKPK*

METHODS TO PREVENT DISULFIDE SCRAMBLING FOR MS-BASED PROTEOMICS

CROSS-REFERENCE TO RELATED APPLICATIONS

This application claims priority to and the benefit of U.S. Provisional Patent Application No. 63/274,256, filed Nov. 1, 2021 which is herein incorporated by reference.

SEQUENCE LISTING

The instant application contains a Sequence Listing which has been submitted electronically in XML format and is hereby incorporated by reference in its entirety. Said XML copy, created on Apr. 5, 2023, is named 070816-02761_10999US01_SL.xml and is 17,936 bytes in size.

FIELD

This application relates to methods for preventing sample-induced disulfide scrambling during characterization of a protein of interest.

BACKGROUND

Mass spectrometry (MS) has become an increasingly important technique to analyze proteins. In popular bottom-up MS-based proteomics, reduction and alkylation are routine steps to facilitate peptide identification. However, side reactions may occur, which compromise the experimental results.

Sample preparation is a critical step in bottom-up MS-based proteomics. One of the key challenges in the use of MS-based proteomics is prevention of disulfide bond scrambling during sample preparation. Numerous methods have been developed, in the past, to address this challenge. It has been noted that temperature, pH, and the availability of free cysteines are critical factors that must be controlled during sample preparation to prevent the formation of non-native disulfide bonds. It is widely accepted that pH tremendously affects disulfide bond or cysteine reactivity, even at room temperature, and must be carefully controlled during sample preparation. The reported methods teach sample preparation at slightly acidic pH, stating that at alkaline pH, free thiols are deprotonated, and the resulting thiolate anions are oxidized or react with adjacent disulfide bonds (thiol/disulfide exchange) to form new, non-native disulfide bonds.

After the low pH protein alkylation, the pH can be increased for protein digestion, which adds an extra step, or the low pH can be maintained for the digestion conditions. Protein digestion entirely under acidic conditions minimize disulfide scrambling, but creates digestion peptide profiles with significant differences (e.g., non-specific cleavages) compared to traditional basic-pH digests. Thus, there is a long felt need in the art for an efficient method for protein preparation, without requiring a low pH protein alkylation.

A method has been developed for characterizing a protein of interest, while preventing the formation of sample preparation-induced disulfide scrambling. The method includes use of a novel alkylation agent, maleimide, during sample preparation to prevent native disulfide disruption. Use of maleimide allows for sample preparation without inducing disulfide scrambling. Use of maleimide also provides a less hydrophobic alkylation agent than N-Ethyl Maleimide (NEM) by having a reagent UV peak that does not interfere with the common peptide peak reporting window. This eliminates the need to use a buffer exchange step after sample alkylation and avoids sample loss.

SUMMARY

Similar to NEM, maleimide is capable of preventing protocol-induced disulfide scrambling when alkylation is performed simultaneously with a denaturing step under acidic conditions (pH<6). After performing the alkylation step under acidic conditions, pH can be safely raised (e.g., to 7.5) for efficient enzymatic digestion with trypsin and/or LysC without inducing additional disulfide scrambling (i.e., free thiols are the major culprit for disulfide scrambling formation during sample prep).

After acidic alkylation, performing a digestion step at similar pH as with traditional non-reduced peptide mapping digests (e.g., using iodoacetamide for cysteine alkylation followed by enzymatic digestion at pH 7.5) creates peptide profiles which are very similar to the traditional digests.

This disclosure provides a method for performing a non-reduced peptide mapping of a protein of interest in a sample, said method comprising contacting said sample to a NEM analog to form an alkylated protein of interest; contacting said alkylated protein of interest to at least one digestive enzyme to form a peptide digest; and subjecting said peptide digest to analysis using liquid chromatography-mass spectrometry to obtain said non-reduced peptide mapping of said protein of interest.

In one aspect, the NEM analog is less hydrophobic than NEM. In another aspect, the NEM analog has a retention time less than the retention time of NEM. In yet another aspect, the NEM analog is maleimide.

In one aspect, the concentration of NEM analog used to contact said sample is about 1 mM to about 10 mM. In another aspect, the concentration of NEM analog used to contact said sample is about 2 mM to about 8 mM. In yet another aspect, the concentration of NEM analog used to contact said sample is about 4 mM.

In one aspect, said NEM analog is contacted with said sample at 50° C. for 30 minutes.

In one aspect, said protein of interest is an antibody. In a particular aspect, said protein of interest is a monoclonal antibody or a bispecific antibody.

In one aspect, the method further comprises contacting said sample to at least one denaturation agent. In a particular aspect, said at least one denaturation agent is urea. In another particular aspect, said urea is present at between about 6 M and about 10 M, optionally wherein said urea is present at about 8 M. In another particular aspect, said denaturation is conducted at about 37° C. or about 50° C.

In one aspect, said at least one digestive enzyme is trypsin. In another aspect, said at least one digestive enzyme is Lys-C. In yet another aspect, said at least one digestive enzyme is Lys-C and trypsin.

In one aspect, said digestion is conducted at a pH between about 7 and about 8. In a particular aspect, said digestion is conducted at a pH between about 7 and about 7.5. In another aspect, said digestion is conducted at a pH between about 5 and about 6. In a particular aspect, said digestion is conducted at a pH between about 5.3 and about 7.

In one aspect, said chromatography step comprises reversed phase liquid chromatography, ion exchange chromatography, size exclusion chromatography, affinity chromatography, hydrophobic interaction chromatography, hydrophilic interaction chromatography, mixed-mode chromatography, or a combination thereof.

In one aspect, said mass spectrometer is an electrospray ionization mass spectrometer, nano-electrospray ionization mass spectrometer, or an Orbitrap-based mass spectrometer, wherein said mass spectrometer is coupled to said liquid chromatography system.

This disclosure provides a method for characterizing a protein of interest in a sample, said method comprising contacting said sample to a NEM analog to form an alkylated protein of interest; contacting said alkylated protein of interest to at least one digestive enzyme to form a peptide digest; and subjecting said peptide digest to analysis using liquid chromatography-mass spectrometry to obtained said non-reduced peptide mapping of said protein of interest.

In one aspect, the NEM analog is less hydrophobic than NEM. In another aspect, the NEM analog has a retention time less than the retention time of NEM. In yet another aspect, the NEM analog is maleimide.

In one aspect, the concentration of NEM analog used to contact said sample is about 1 mM to about 10 mM. In another aspect, the concentration of NEM analog used to contact said sample is about 2 mM to about 8 mM. In yet another aspect, the concentration of NEM analog used to contact said sample is about 4 mM.

In one aspect, said NEM analog is contacted with said sample at 50° C. for 30 minutes.

In one aspect, said protein of interest is an antibody. In a particular aspect, said protein of interest is a monoclonal antibody or a bispecific antibody.

In one aspect, the method further comprising contacting said sample to at least one denaturation agent. In a particular aspect, said at least one denaturation agent is urea. In another particular aspect, said urea is present at between about 6 M and about 10 M, optionally wherein said urea is present at about 8 M. In another particular aspect, wherein said denaturation is conducted at about 3° C. or about 50° C.

In one aspect, said at least one digestive enzyme is trypsin. In another aspect, said at least one digestive enzyme is Lys-C. In yet another aspect, said at least one digestive enzyme is Lys-C and trypsin.

In one aspect, said digestion is conducted at a pH between about 7 and about 8. In a particular aspect, said digestion is conducted at a pH between about 7 and about 7.5. In another aspect, said digestion is conducted at a pH between about 5 and about 6. In a particular aspect, said digestion is conducted at a pH between about 5.3 and about 7.

In one aspect, said chromatography step comprises reversed phase liquid chromatography, ion exchange chromatography, size exclusion chromatography, affinity chromatography, hydrophobic interaction chromatography, hydrophilic interaction chromatography, mixed-mode chromatography, or a combination thereof.

In one aspect, said mass spectrometer is an electrospray ionization mass spectrometer, nano-electrospray ionization mass spectrometer, or an Orbitrap-based mass spectrometer, wherein said mass spectrometer is coupled to said liquid chromatography system.

This disclosure provides a method for characterizing a protein of interest in a sample, said method comprising contacting said sample to maleimide analog to form an alkylated protein of interest; contacting said alkylated protein of interest to at least one digestive enzyme to form a peptide digest; and subjecting said peptide digest to analysis using liquid chromatography-mass spectrometry to obtained said non-reduced peptide mapping of said protein of interest.

In one aspect, the concentration of maleimide used to contact said sample is about 1 mM to about 10 mM. In another aspect, the concentration of maleimide used to contact said sample is about 2 mM to about 8 mM. In yet another aspect, the concentration of maleimide used to contact said sample is about 4 mM.

In one aspect, said maleimide is contacted with said sample at 50° C. for 30 minutes.

In one aspect, said protein of interest is an antibody. In a particular aspect, said protein of interest is a monoclonal antibody or a bispecific antibody.

In one aspect, the method further comprising contacting said sample to at least one denaturation agent. In a particular aspect, said at least one denaturation agent is urea. In another particular aspect, said urea is present at between about 6 M and about 10 M, optionally wherein said urea is present at about 8 M. In another particular aspect, wherein said denaturation is conducted at about 37° C. or about 50° C.

In one aspect, said at least one digestive enzyme is trypsin. In another aspect, said at least one digestive enzyme is Lys-C. In yet another aspect, said at least one digestive enzyme is Lys-C and trypsin.

In one aspect, said digestion is conducted at a pH between about 7 and about 8. In a particular aspect, said digestion is conducted at a pH between about 7 and about 7.5. In another aspect, said digestion is conducted at a pH between about 5 and about 6. In a particular aspect, said digestion is conducted at a pH between about 5.3 and about 7.

In one aspect, said chromatography step comprises reversed phase liquid chromatography, ion exchange chromatography, size exclusion chromatography, affinity chromatography, hydrophobic interaction chromatography, hydrophilic interaction chromatography, mixed-mode chromatography, or a combination thereof.

In one aspect, said mass spectrometer is an electrospray ionization mass spectrometer, nano-electrospray ionization mass spectrometer, or an Orbitrap-based mass spectrometer, wherein said mass spectrometer is coupled to said liquid chromatography system.

BRIEF DESCRIPTION OF THE DRAWINGS

FIG. 6A shows a normalized peak area of alkylated free thiols (STSESTAALGCLVK (SEQ ID NO.: 2) and TYTCNVDHKPSNTK (SEQ ID NO.: 3)) from low pH non-reduced peptide mapping analysis of mAb3 using NEM, maleimide, N-hydroxy maleimide and maleamide according to an exemplary embodiment.

FIG. 6B shows a normalized peak area of non-alkylated free thiols (STSESTAALGCLVK (SEQ ID NO.: 2) and TYTCNVDHKPSNTK (SEQ ID NO.: 3)) from low pH non-reduced peptide mapping analysis of mAb3 using NEM, maleimide, N-hydroxy maleimide and maleamide according to an exemplary embodiment.

DETAILED DESCRIPTION

Figure 1:
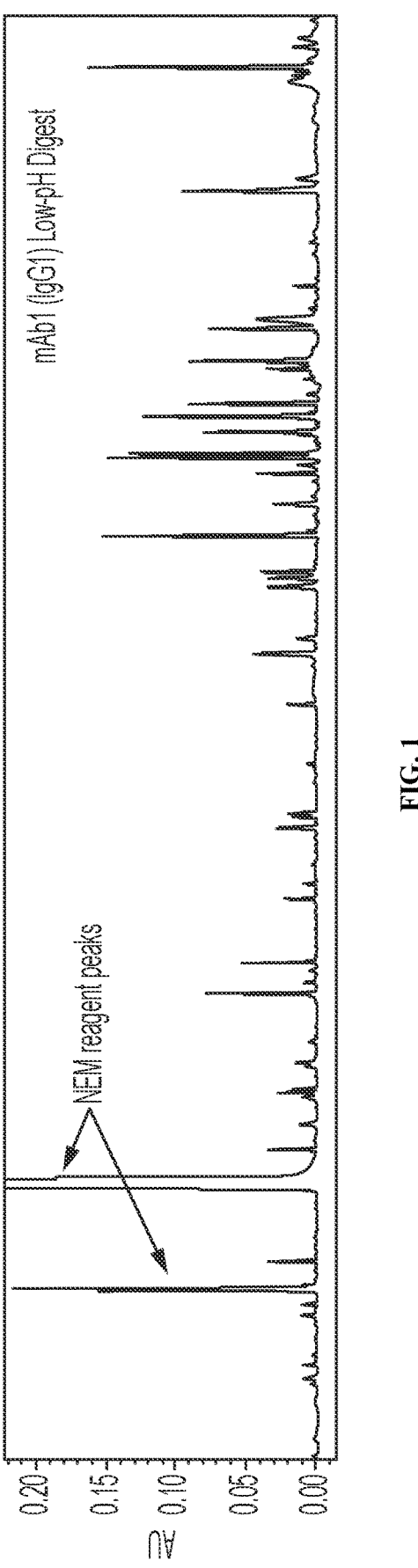
FIG. 1 shows a UV chromatogram of mAb 1 obtained from non-reduced peptide mapping analysis of mAb 1 prepared in low pH non-reducing peptide mapping conditions according to an exemplary embodiment.

Characterization of monoclonal antibodies' (mAbs) product quality attributes (PQAs) is important due to the large size and complex heterogeneity of this increasingly popular class of therapeutics. One such PQA is the proper formation of classical disulfide bond structures. Deviations from the canonical IgG disulfide conformation, including non-classical disulfide bonding (scrambling), may negatively impact a mAb's structure, stability, and biological efficacy (Zhang et al., 2011, *Biotechnol Adv,* 29(6):923-9; Liu et al., 2012, *MAbs,* 4(1):17-23; Liu et al., 2007, *Biotechnol Lett,* 29(11): 611-22; Brych et al., 2010, *J Pharm Sci,* 99(2):764-81; Mamathambika and Bardwell, 2008, *Annu Rev Cell Dev Biol,* 24:211-35; Zhang et al., 2012, *Anal Chem,* 84(16): 7112-23; Van Buren et al., 2009, *J Pharm Sci,* 98(9):3013-30; Zhang et al., 2019, *Protein Expr Purif,* 164:105459).

Disulfide bond conformation is highly conserved in accordance with each IgG subclass (Milstein, 1966, *Biochem J,* 101(2):338-51; Pinck and Milstein, 1967, *Nature,* 216 (5118):941-2; Frangione and Milstein, 1968, *J Mol Biol,* 33(3):893-906; Frangione et al., 1969, *Nature,* 221(5176): 145-8). For example, IgG1 molecules have a four-chain structure composed of two heavy chains (HCs) and two light chains (LCs) covalently linked by inter-chain disulfide bonds, as shown in FIG. 1A. In addition to the inter-chain disulfide bonds, one intra-chain disulfide bond is present and is shielded within each (3-barrel domain of the HC and LC polypeptides (Zhang et al., 2002, *Anal Biochem,* 311(1):1-9). In the hinge region, the two HCs are covalently linked by two inter-chain disulfide bonds.

A typical therapeutic mAb has a molecular weight of about 140 kDa, rendering traditional disulfide bond mapping methods less applicable, such as NMR (Klaus et al., 1993, *J Mol Biol,* 232(3):897-906), X-ray crystallography (Jones et al., 1997, *Methods Enzymol,* 277:173-208), and Edman sequencing (Haniu et al., 1994, *Int J Pept Protein Res,* 43(1):81-6). The rapid evolution of liquid chromatography-mass spectrometry (LC-MS) and its successful implementation in biomolecule analysis has enabled in-depth profiling of mAb PQAs, including canonical disulfide bond formation and identification of non-classical disulfide features like disulfide bond scrambling, free thiol, and trisulfide bond formation. The most common LC-MS approach to study mAb disulfide bonds, known as non-reduced peptide mapping, is a modified version of the conventional reduced peptide mapping approach with no disulfide reduction step and lower amount of thiol alkylating agent (Li et al., 2015, *State-of-the-Art and Emerging Technologies for Therapeutic Monoclonal Antibody Characterization Volume 2. Biopharmaceutical Characterization: The NISTmAb Case Study,* pp. 119-183; Formolo et al., 2015, *State-of-the-Art and Emerging Technologies for Therapeutic Monoclonal Antibody Characterization Volume 2. Biopharmaceutical Characterization: The NISTmAb Case Study,* pp. 1-62). Trypsin is the most commonly used digestive enzyme due to its high specificity, efficiency, and propensity to generate peptides of appropriate length for MS analysis. The resulting method enzymatically cleaves the mAb into peptide species, with any potential disulfide bonds remaining intact. All peptides are then analyzed by LC-MS, where a UV detector generates a "peptide fingerprint" by measuring the UV absorbance of the eluting analytes according to their retention times, and a mass spectrometer ionizes these analytes and records their mass-to-charge ratios (m/z). High-resolution accurate-mass (HRAM) mass spectrometers with tandem mass spectrometry ($MS^2$) capabilities coupled to advanced protein/peptide identification algorithms like Byonic have simplified peptide mapping analysis so that even sensitive identification of disulfide-linked peptides and site-specific identification of free thiol are now routine.

The high selectivity and sensitivity of non-reduced peptide mapping inherits a disadvantage associated with reduced peptide mapping: experimental conditions and reagents can sometimes induce confounding chemical modifications into peptide sequences if the method is not thoroughly optimized and carefully developed. For non-reduced peptide mapping, scrambled disulfide artifacts were found to be associated with sample preparation steps, such as denaturation by heating and/or enzymatic digestion conditions at alkaline pH. These experimentally introduced scrambled disulfide artifacts may lead to false interpretations or conclusions regarding their pre-existing levels in the native therapeutic mAbs (Liu et al., 2007; Zhang et al., 2002, *Anal Biochem,* 311(1):1-9; Wu and Watson, 1997, *Protein Sci,* 6(2):391-8).

To reduce disulfide scrambling artifacts during non-reduced analyses, several strategies have been developed. The simplest approach is to alkylate free cysteine using an excess amount of iodoacetamide, which essentially caps all endogenous free thiols as well as artifact thiols before any scrambling can occur. However, this method fails to prevent undesired disulfide disruption, and a large excess of iodoacetamide causes nonspecific labeling of other residues that are sometimes visible in the UV chromatogram (Boja and Fales, 2001, *Anal Chem,* 73(15): 3576-82; Muller and Winter, 2017, *Mol Cell Proteomics,* 16(7):1173-1187).

Another strategy to minimize disulfide scrambling is to conduct denaturation and digestion at acidic pH while capping free thiol with N-ethylmaleimide (NEM) due to its high reactivity in acidic conditions (Ryle et al., 1955, *Biochem J,* 60(4):541-56; Robotham and Kelly, 2019, *MAbs,* 11(4):757-766). To circumvent the low activity of trypsin in acidic pH and bolster digestion efficiency, alternative enzymes like pepsin with acceptable activities at low pH have been used, but the non-specific ragged cleavages makes the assignment of disulfide bonds rather complex.

Another solution, pioneered by Promega™ and produced as a digestion kit called AccuMAP™, utilizes rLys-C and trypsin at acidic pH to efficiently cleave arginine and lysine residues while minimizing scrambling. Since trypsin and other proteases commonly used in peptide mapping sample preparation favor alkaline pH in order to efficiently digest proteins, so the AccuMAP™ digestion kit, the kit supplements trypsin with a special, low pH resistant recombinant Lys-C (rLys-C) protease. However, digestion specificity and efficiency still suffer, and a one-enzyme approach that minimizes disulfide scrambling with the high digestion specificity and efficiency of trypsin is desirable to ensure assay reproducibility and robustness.

The disclosure herein provides an elegant solution to prevent disulfide bonds in proteins from scrambling during non-reduced tryptic digestion conditions. A standard peptide mapping protocol was modified by using an analog of NEM (NEM) to alkylation of native free thiols. Five in-house IgG1 and IgG4 mAbs were selected in this study because a relatively high level of scrambled disulfide bonds was identified in the samples when a conventional non-reduced peptide mapping protocol was implemented. These mAbs were used to demonstrate that adding maleimide (a NEM analog which is less hydrophobic) to non-reduced peptide mapping protocols eliminates disulfide scrambling artifacts. The disclosure also discusses a 'half-acidic' digest condition which combines the use of maleimide at acidic conditions and digestion at basic conditions. These methods enable confident analysis of proteins while maintaining the advantages of tryptic digestion.

Unless described otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described. All publications mentioned are hereby incorporated by reference.

The term "a" should be understood to mean "at least one"; and the terms "about" and "approximately" should be understood to permit standard variation as would be understood by those of ordinary skill in the art; and where ranges are provided, endpoints are included.

In some exemplary embodiments, the disclosure provides a method for characterizing a protein of interest.

As used herein, the term "protein" or "protein of interest" includes any amino acid polymer having covalently linked amide bonds. Proteins comprise one or more amino acid polymer chains, generally known in the art as "polypeptides." "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides' refers to a non-naturally occurring peptide or polypeptide. Synthetic peptides or polypeptides can be synthesized, for example, using an automated polypeptide synthesizer.

Various solid phase peptide synthesis methods are known. A protein may contain one or multiple polypeptides to form a single functioning biomolecule. A protein can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. In another exemplary aspect, a protein can include antibody fragments, nanobodies, recombinant antibody chimeras, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO—K1 cells). For a review discussing biotherapeutic proteins and their production, see Ghaderi et al., "Production platforms for biotherapeutic glycoproteins. Occurrence, impact, and challenges of non-human sialylation," (BIO-TECHNOL. GENET. ENG. REV. 147-175 (2012)). In some exemplary embodiments, proteins comprise modifications, adducts, and other covalently linked moieties. Those modifications, adducts and moieties include for example avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as, globular proteins and fibrous proteins; conjugated proteins, such as nucleoproteins, glycoproteins, mucoproteins, chromoproteins, phosphoproteins, metalloproteins, and lipoproteins; and derived proteins, such as primary derived proteins and secondary derived proteins.

In some exemplary embodiments, the protein can be an antibody, a bispecific antibody, a multispecific antibody, antibody fragment, monoclonal antibody, or an Fc fusion protein.

The term "antibody," as used herein includes immunoglobulin molecules comprising four polypeptide chains, two heavy (H) chains and two light (L) chains inter-connected by disulfide bonds, as well as multimers thereof (e.g., IgM).

Each heavy chain comprises a heavy chain variable region (abbreviated herein as HCVR or $V_H$) and a heavy chain constant region. The heavy chain constant region comprises three domains, $C_H1$, $C_{H2}$ and $C_H3$. Each light chain comprises a light chain variable region (abbreviated herein as LCVR or $V_L$) and a light chain constant region. The light chain constant region comprises one domain ($C_{L1}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different exemplary embodiments, the FRs of the anti-big-ET-1 antibody (or antigen-binding portion thereof) may be identical to the human germline sequences, or may be naturally or artificially modified. An amino acid consensus sequence may be defined based on a side-by-side analysis of two or more CDRs. The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a Fc fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. An antibody fragment may be produced by various means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

The term "Fc fusion proteins" as used herein includes part or all of two or more proteins, one of which is an Fc portion of an immunoglobulin molecule, that are not fused in their natural state. Preparation of fusion proteins comprising certain heterologous polypeptides fused to various portions of antibody-derived polypeptides (including the Fc domain) has been described, e.g., by Ashkenazi et al., Proc. Natl. Acad. ScL USA 88: 10535, 1991; Byrn et al., Nature 344:677, 1990; and Hollenbaugh et al., "Construction of Immunoglobulin Fusion Proteins," in Current Protocols in Immunology, Suppl. 4, pages 10.19.1-10.19.11, 1992. "Receptor Fc fusion proteins" comprise one or more of one or more extracellular domain(s) of a receptor coupled to an Fc moiety, which in some embodiments comprises a hinge region followed by a CH2 and CH3 domain of an immunoglobulin. In some embodiments, the Fc-fusion protein contains two or more distinct receptor chains that bind to a single or more than one ligand(s). For example, an Fc-fusion protein is a trap, such as for example an IL-1 trap (e.g., Rilonacept, which contains the IL-1 RAcP ligand binding region fused to the IL-1R1 extracellular region fused to Fc of hIgG1; see U.S. Pat. No. 6,927,004, which is herein incorporated by reference in its entirety), or a VEGF Trap (e.g., Aflibercept, which contains the Ig domain 2 of the VEGF receptor Flt1 fused to the Ig domain 3 of the VEGF receptor Flk1 fused to Fc of hIgG1; e.g., see U.S. Pat. Nos. 7,087,411 and 7,279,159, which are herein incorporated by reference in their entirety).

As used herein, the general term "post-translational modifications" or "PTMs" refers to covalent modifications that polypeptides undergo, either during (co-translational modification) or after (post-translational modification) their ribosomal synthesis. PTMs are generally introduced by specific enzymes or enzyme pathways. Many occur at the site of a specific characteristic protein sequence (signature sequence) within the protein backbone. Several hundred PTMs have been recorded, and these modifications invariably influence some aspect of a protein's structure or function (Walsh, G. "Proteins" (2014) second edition, published by Wiley and Sons, Ltd., ISBN: 9780470669853). The various post-translational modifications include, but are not limited to, cleavage, N-terminal extensions, protein degradation, acylation of the N-terminus, biotinylation (acylation of lysine residues with a biotin), amidation of the C-terminal, glycosylation, iodination, covalent attachment of prosthetic groups, acetylation (the addition of an acetyl group, usually at the N-terminus of the protein), alkylation (the addition of an alkyl group (e.g. methyl, ethyl, propyl) usually at lysine or arginine residues), methylation, adenylation, ADP-ribosylation, covalent cross links within, or between, polypeptide chains, sulfonation, prenylation, Vitamin C dependent modifications (proline and lysine hydroxylations and carboxy terminal amidation), Vitamin K dependent modification wherein Vitamin K is a cofactor in the carboxylation of glutamic acid residues resulting in the formation of a γ-carboxyglutamate (a glu residue), glutamylation (covalent linkage of glutamic acid residues), glycylation (covalent linkage glycine residues), glycosylation (addition of a glycosyl group to either asparagine, hydroxylysine, serine, or threonine, resulting in a glycoprotein), isoprenylation (addition of an isoprenoid group such as farnesol and geranylgeraniol), lipoylation (attachment of a lipoate functionality), phosphopantetheinylation (addition of a 4'-phosphopantetheinyl moiety from coenzyme A, as in fatty acid, polyketide, non-ribosomal peptide and leucine biosynthesis), phosphorylation (addition of a phosphate group, usually to serine, tyrosine, threonine or histidine), and sulfation (addition of a sulfate group, usually to a tyrosine residue). The post-translational modifications that change the chemical nature of amino acids include, but are not limited to, citrullination (the conversion of arginine to citrulline by deimination), and deamidation (the conversion of glutamine to glutamic acid or asparagine to aspartic acid). The post-translational modifications that involve structural changes include, but are not limited to, formation of disulfide bridges (covalent linkage of two cysteine amino acids) and proteolytic cleavage (cleavage of a protein at a peptide bond). Certain post-translational modifications involve the addition of other proteins or peptides, such as ISGylation (covalent linkage to the ISG15 protein (Interferon-Stimulated Gene)), SUMOylation (covalent linkage to the SUMO protein (Small Ubiquitin-related MOdifier)) and ubiquitination (covalent linkage to the protein ubiquitin). See European Bioinformatics Institute Protein Information ResourceSIB Swiss Institute of Bioinformatics, EUROPEAN BIOINFORMATICS INSTITUTE DRS—DROSOMYCIN PRECURSOR—DROSOPHILA MELANOGASTER (FRUIT FLY)—DRS GENE & PROTEIN, http://www.uniprot.org/docs/ptm-list (last visited Jan. 15, 2019) for a more detailed controlled vocabulary of PTMs curated by UniProt.

As used herein, the term "chromatography" refers to a process in which a chemical mixture carried by a liquid or gas can be separated into components as a result of differential distribution of the chemical entities as they flow around or over a stationary liquid or solid phase. Non-limiting examples of chromatography include traditional reversed-phased (RP), ion exchange (IEX), mixed mode chromatography and normal phase chromatography (NP).

As used herein, the term "mass spectrometer" includes a device capable of identifying specific molecular species and measuring their accurate masses. The term is meant to include any molecular detector into which a polypeptide or peptide may be eluted for detection and/or characterization. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization). The choice of ion source depends heavily on the application.

As used herein, the term "mass analyzer" includes a device that can separate species, that is, atoms, molecules, or clusters, according to their mass. Non-limiting examples of mass analyzers that could be employed for fast protein sequencing are time-of-flight (TOF), magnetic/electric sector, quadrupole mass filter (Q), quadrupole ion trap (QIT), orbitrap, Fourier transform ion cyclotron resonance (FTICR), and also the technique of accelerator mass spectrometry (AMS).

In some exemplary embodiments, automated iterative MS/MS can be performed under native conditions. As used herein, the term "native conditions" can include performing mass spectrometry under conditions that preserve non-covalent interactions in an analyte. For a detailed review on native MS, refer to the review: Elisabetta Boeri Erba & Carlo Pe-tosa, The emerging role of native mass spectrometry in characterizing the structure and dynamics of macromolecular complexes, 24 PROTEIN SCIENCE 1176-1192 (2015).

In some exemplary embodiments, the mass spectrometer can be a tandem mass spectrometer.

As used herein, the term "tandem mass spectrometry" includes a technique where structural information on sample molecules is obtained by using multiple stages of mass selection and mass separation. A prerequisite is that the sample molecules can be transferred into gas phase and ionized intact and that they can be induced to fall apart in some predictable and controllable fashion after the first mass selection step. Multistage MS/MS, or $MS^n$, can be performed by first selecting and isolating a precursor ion ($MS^2$), fragmenting it, isolating a primary fragment ion ($MS^3$), fragmenting it, isolating a secondary fragment ($MS^4$), and so on as long as one can obtain meaningful information or the fragment ion signal is detectable. Tandem MS have been successfully performed with a wide variety of analyzer combinations. What analyzers to combine for a certain application is determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers. A tandem-in-space mass spectrometer comprises an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition. In tandem-in-time mass spectrometer ions produced in the ion source can be trapped, isolated, fragmented, and m/z separated in the same physical device.

The peptides identified by the mass spectrometer can be used as surrogate representatives of the intact protein and their post-translational modifications. They can be used for protein characterization by correlating experimental and theoretical MS/MS data, the latter generated from possible peptides in a protein sequence database. The characterization can include, but is not limited, to sequencing amino acids of the protein fragments, determining protein sequencing, determining protein de novo sequencing, locating post-translational modifications, or identifying post translational modifications, or comparability analysis, or combinations thereof.

As used herein, the term "database" refers to a compiled collection of protein sequences that may possibly exist in a sample, for example in the form of a file in a FASTA format. Relevant protein sequences may be derived from cDNA sequences of a species being studied. Public databases that may be used to search for relevant protein sequences included databases hosted by, for example, Uniprot or Swiss-prot. Databases may be searched using what are herein referred to as "bioinformatics tools." Bioinformatics tools provide the capacity to search uninterpreted MS/MS spectra against all possible sequences in the database(s), and provide interpreted (annotated) MS/MS spectra as an output. Non-limiting examples of such tools are Mascot (www.matrixscience.com), Spectrum Mill (www.chem.agilent.com), PLGS (www.waters.com), PEAKS (www.bioinformaticssolutions.com), Proteinpilot (download.appliedbiosystems.com//proteinpilot), Phenyx (www.phenyx-ms.com), Sorcerer (www.sagenresearch.com), OMS SA (www.pubchem.ncbi.nlm.nih.gov/omssa/), X!Tandem (www.thegpm.org/TANDEM/), Protein Prospector (prospector.ucsfedu/prospector/mshome.htm), Byonic (www.protein-metrics.com/products/byonic) or Sequest (fields.s-cripps.edu/sequest).

As used herein, the term "protein alkylating agent" or "alkylation agent" refers to an agent used for alkylating certain free amino acid residues in a protein. Non-limiting examples of commercial protein alkylating agents are iodo-acetamide (IOA/IAA), chloroacetamide (CAA), acrylamide (AA), N-ethylmaleimide (NEM), methyl methanethio-sulfonate (MMTS), and 4-vinylpyridine or combinations thereof.

In some embodiments, the sample comprising the protein of interest in a sample can be treated by adding a reducing agent to the sample.

As used herein, "protein denaturing" or "denaturation" can refer to a process in which the three-dimensional shape of a molecule is changed from its native state. Protein denaturation can be carried out using a protein denaturing agent. Non-limiting examples of a protein denaturing agent include heat, high or low pH, reducing agents like DTT, or exposure to chaotropic agents. Several chaotropic agents can be used as protein denaturing agents. Chaotropic solutes increase the entropy of the system by interfering with intramolecular interactions mediated by non-covalent forces such as hydrogen bonds, van der Waals forces, and hydro-phobic effects. Non-limiting examples of chaotropic agents include butanol, ethanol, guanidinium chloride, lithium per-chlorate, lithium acetate, magnesium chloride, phenol, pro-panol, sodium dodecyl sulfate, thiourea, N-lauroylsarcosine, urea, and salts thereof.

As used herein, the term "digestion" refers to hydrolysis of one or more peptide bonds of a protein. There are several approaches to carrying out digestion of a protein in a sample using an appropriate hydrolyzing agent, for example, enzy-matic digestion or non-enzymatic digestion. Digestion of a protein into constituent peptides can produce a "peptide digest" that can further be analyzed using peptide mapping analysis.

As used herein, the term "digestive enzyme" refers to any of a large number of different agents that can perform digestion of a protein. Non-limiting examples of hydrolyz-ing agents that can carry out enzymatic digestion include protease from *Aspergillus Saitoi*, elastase, subtilisin, pro-tease XIII, pepsin, trypsin, Tryp-N, chymotrypsin, aspergil-lopepsin I, LysN protease (Lys-N), LysC endoproteinase (Lys-C), endoproteinase Asp-N (Asp-N), endoproteinase Arg-C (Arg-C), endoproteinase Glu-C (Glu-C) or outer membrane protein T (OmpT), immunoglobulin-degrading enzyme of *Streptococcus pyogenes* (IdeS), thermolysin, papain, pronase, V8 protease or biologically active frag-ments or homologs thereof or combinations thereof. For a recent review discussing the available techniques for protein digestion see Switazar et al., "Protein Digestion: An Over-view of the Available Techniques and Recent Develop-ments" (Linda Switzar, Martin Giera & Wilfried M. A. Niessen, Protein Digestion: An Overview of the Available Techniques and Recent Developments, 12 JOURNAL OF PROTEOME RESEARCH 1067-1077 (2013)).

As used herein, a "sample" can be obtained from any step of a bioprocess, such as cell culture fluid (CCF), harvested cell culture fluid (HCCF), any step in the downstream processing, drug substance (DS), or a drug product (DP) comprising the final formulated product. In some specific exemplary embodiments, the sample can be selected from any step of the downstream process of clarification, chro-matographic production, or filtration.

The method of the present invention may be applied to any protein featuring disulfide bonds. In some exemplary embodiments, a particular application involves analysis of a protein of interest that is an antibody. In some exemplary embodiments, the protein of interest is a monoclonal anti-body. In some exemplary embodiments, the protein of interest is a bispecific antibody. In some exemplary embodi-ments, the protein of interest is a recombinant protein.

A variety of denaturation agents may be used in the sample preparation step of the method of the present inven-tion, for example, guanidine hydrochloride or urea. In some exemplary embodiments, the denaturation agent is urea. Urea may be used at a concentration of about 6 M, about 6.1 M, about 6.2 M, about 6.3 M, about 6.4 M, about 6.5 M, about 6.6 M, about 6.7 M, about 6.8 M, about 6.9 M, about 7 M, about 7.1 M, about 7.2 M, about 7.3 M, about 7.4 M, about 7.5 M, about 7.6 M, about 7.7 M, about 7.8 M, about 7.9 M, about 8 M, about 8.1 M, about 8.2 M, about 8.3 M, about 8.4 M, about 8.5 M, about 8.6 M, about 8.7 M, about 8.8 M, about 8.9 M, about 9 M, about 9.1 M, about 9.2 M, about 9.3 M, about 9.4 M, about 9.5 M, about 9.6 M, about 9.7 M, about 9.8 M, about 9.9 M, or about 10 M. In some exemplary embodiments, an optimal concentration of urea is about 8 M.

Denaturation may be conducted in a variety of conditions. Acidic pH conditions have been used to reduce disulfide scrambling.

In some exemplary embodiments, the alkylation agent used is a NEM analog, such as maleimide. Maleimide can be used at a relatively wide range of concentrations. The concentration of maleimide may be about 1 mM, about 1.1 mM about 1.2 mM, about 1.3 mM, about 1.4 mM, about 1.5 mM, about 1.6 mM, about 1.7 mM, about 1.8 mM, about 1.9 mM, about 2 mM, about 2.1 mM, about 2.2 mM, about 2.3 mM, about 2.4 mM, about 2.5 mM, about 2.6 mM, about 2.7 mM, about 2.8 mM, about 2.9 mM, about 3 mM, about 3.1 mM, about 3.2 mM, about 3.3 mM, about 3.4 mM, about 3.5 mM, about 3.6 mM, about 3.7 mM, about 3.8 mM, about 3.9 mM, about 4 mM, about 4.5 mM, about 5 mM, about 5.5 mM, about 6 mM, about 6.5 mM, about 7 mM, about 7.5 mM, about 8 mM, about 8.5 mM, about 9 mM, about 9.5 mM, or about 10 mM. In some exemplary embodiments, an optimal concentration of maleimide is about 4.0 mM.

Digestive enzymes used for non-reduced peptide mapping may include, for example, one or more of trypsin, pepsin, or LysC. In some exemplary embodiments, the digestive enzyme is trypsin. Trypsin may be used at an enzyme:substrate ratio of about 1:5, about 1:5.5, about 1:6, about 1:6.5, about 1:7, about 1:7.5, about 1:8, about 1:8.5, about 1:9, about 1:9.5, about 1:10, about 1:10.5, about 1:11, about 1:11.5, about 1:12, about 1:12.5, about 1:13, about 1:13.5, about 1:14, about 1:14.5, about 1:15, about 1:16, about 1:17, about 1:18, about 1:19, or about 1:20. In some exemplary embodiments, an optimal enzyme:substrate ratio of trypsin is about 1:10.

Digestion may be conducted at a pH of about 5, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0. In some exemplary embodiments, an optimal pH for digestion is about 7.5.

While the method described above recites the character-ization of at least one disulfide bond of a protein of interest, it should be understood that this method may be extended to a variety of applications. It is further understood that "characterizing" at least one protein of interest may include, for example, identifying, quantifying, and/or comparing said at least one protein of interest.

It is understood that the present invention is not limited to any of the aforesaid protein(s), protein(s) of interest, antibody(s), protein alkylating agent(s), protein denaturing agent(s), protein reducing agent(s), digestive enzyme(s), sample(s), chromatographic method(s), mass spectrometer(s), database(s), bioinformatics tool(s), pH, temperature(s), or concentration(s), and any protein(s), protein(s) of interest, antibody(s), protein alkylating agent(s), protein denaturing agent(s), protein reducing agent(s), digestive enzyme(s), sample(s), chromatographic method(s), mass spectrometer(s), database(s), bioinformatics tool(s), pH, temperature(s), or concentration(s) can be selected by any suitable means.

The consecutive labeling of method steps as provided herein with numbers and/or letters is not meant to limit the method or any embodiments thereof to the particular indicated order.

Various publications, including patents, patent applications, published patent applications, accession numbers, technical articles and scholarly articles are cited throughout the specification. Each of these cited references is herein incorporated by reference, in its entirety and for all purposes.

The disclosure will be more fully understood by reference to the following Examples, which are provided to describe the disclosure in greater detail. They are intended to illustrate examples and should not be construed as limiting the scope of the disclosure.

EXAMPLES

Materials.

Trifluoroacetic acid (TFA) and acetonitrile were purchased from Thermo Fisher Scientific (Rockford, IL). Urea, tris(2-carboxyethyl) phosphine hydrochloride (TCEP-HCl) and cystamine dihydrochloride were purchased from Sigma-Aldrich (St. Louis, MO). AccuMap low pH protein digestion kit and mass spectrometry grade Trypsin Platinum were purchased from Promega (Madison, WI). Tris-HCl buffer, pH 7.5 was obtained from Invitrogen (Carlsbad, CA). Purified monoclonal antibodies were produced internally by Regeneron (Tarrytown, NY).

Regular Non-Reducing Peptide Mapping Method.

For regular non-reduced peptide mapping sample preparation, a 200 μg aliquot of each mAb sample was diluted to about 3.3 μg/μL by adding 8 M urea in 100 mM Tris-HCl solution. After sample dilution, protein concentration was measured using a NanoDrop 2000 (Thermo Scientific, MA) UV-Vis spectrophotometer. A 100 μg aliquot of each sample was alkylated with 2.5 mM iodoacetamide and incubated at 50° C. for 30 minutes in the dark. Each sample was then diluted 8 times with 100 mM Tris-HCl, pH 7.5 and digested with Trypsin+LysC at 37° C. for 3 hours. The digestion was quenched by adding TFA to a final concentration of 0.3%.

Low pH Non-Reducing Peptide Mapping Method.

The AccuMAP low pH protein digestion kit from Promega was used for low pH peptide mapping sample preparation. The protocol followed the manufacturer's technical manual with minor modifications.

(1) Blocking Free Cysteines: 5 μl of protein solution (50 μg of protein) was added to 20 μl of AccuMAP™ Denaturing Solution. To this, 6 μl of AccuMAP™ 10× Low pH Reaction Buffer and 2 μl of 200 mM NEM was mixed and incubated for 30 minutes at 37° C. (2) Predigestion: 25 μl of AccuMAP™ Low pH Resistant rLys-C was added, mixed and incubated for 4 hours at 37° C. The pH during these steps was maintained at around 5.7. (3) Digestion: 30 μl of AccuMAP™ 10× Low pH Reaction Buffer was added. To this, AccuMAP™ Low pH Resistant rLys-C or AccuMAP™ Modified Trypsin and AccuMAP™ Low pH Resistant rLys-C were added as follows: Digestion with AccuMAP™ Low pH Resistant rLys-C; 207 μl of NANOpure® water and 25 μl of AccuMAP™ Low pH Resistant rLys-C was added, mixed and incubated overnight at 37° C. Digestion with AccuMAP™ Modified Trypsin and AccuMAP™ Low pH Resistant rLys-C: 187 μl of NANOpure® water and 25 μl of AccuMAP™ Low pH Resistant rLys-C was added, mixed and incubated overnight at 37° C. In the morning, 20 μl of AccuMAP™ Modified Trypsin was added, mixed and incubated for 3 hours at 37° C. (longer incubation with trypsin is not recommended as trypsin could generate semi-tryptic peptides, which contribute to baseline noise). (4) Termination of the Reaction: TFA was added to a final concentration of 2%. A small amount of sample was checked with pH paper to ensure the reaction is properly acidified. The pH during these steps was maintained at around 5.3.

LC/UV-MS Analysis:

A Waters ACQUITY UPLC I-Class system coupled to a Thermo Scientific Q Exactive Plus mass spectrometer was used to analyze the non-reduced digested samples. The tryptic peptide mixture was separated by a Waters ACQUITY UPLC BEH® 130 C18 column (1.7 μm, 2.1 mm×150 mm) at a flow rate of 0.25 mL/minute. Mobile phase A was 0.05% TFA in water and mobile phase B was 0.045% TFA in acetonitrile. The gradient was held at 0.1% B for the first 5 minutes and then increased to 26% B in 55 minutes followed by another increase to 34.5% B in 35 minutes. The column was equilibrated with 99.9% mobile phase A prior to sample injection, with the column temperature maintained at 40° C. The MS data were acquired on a Thermo Scientific Q Exactive Plus mass spectrometer from m/z 300-2000 at a resolution of 70 k (at m/z 400), followed by five data-dependent MS/MS scans at a resolution of 17.5 k. MS full scans were set at $1 \times 10^6$ automated gain control (AGC) and a maximum injection time of 50 ms. $MS^2$ fragmentation was performed using HCD with a normalized collision energy of 28% at a $1 \times 10^5$ AGC, and a maximum injection time of 100 ms. Dynamic exclusion duration was set to 15 seconds with a single repeat count.

Data Analysis.

All peptide identity assignments and post-translational modification identifications were performed using Protein Metrics Byonic™ (version 3.11.3) by searching the raw files against the mAb protein sequence. The preliminary list of unique peptides was generated by filtering against a 1% FDR. The list of precursors and the original searching results as a spectra library were then imported into Skyline Daily software (University of Washington, WA) for a full scan $(MS^1)$-based final ID validation. The peak area was extracted by summing all charge states through Skyline software.

Example 1. Non-Reducing Peptide Mapping Using the Low-pH Digestion Protocol

Protein characterization of mAb 1 (IgG1 antibody) and mAb2 (IgG4 antibody) was carried out using the low pH digestion protocol as published by Promega's AccuMAP low pH digestion product.

Figure 2:
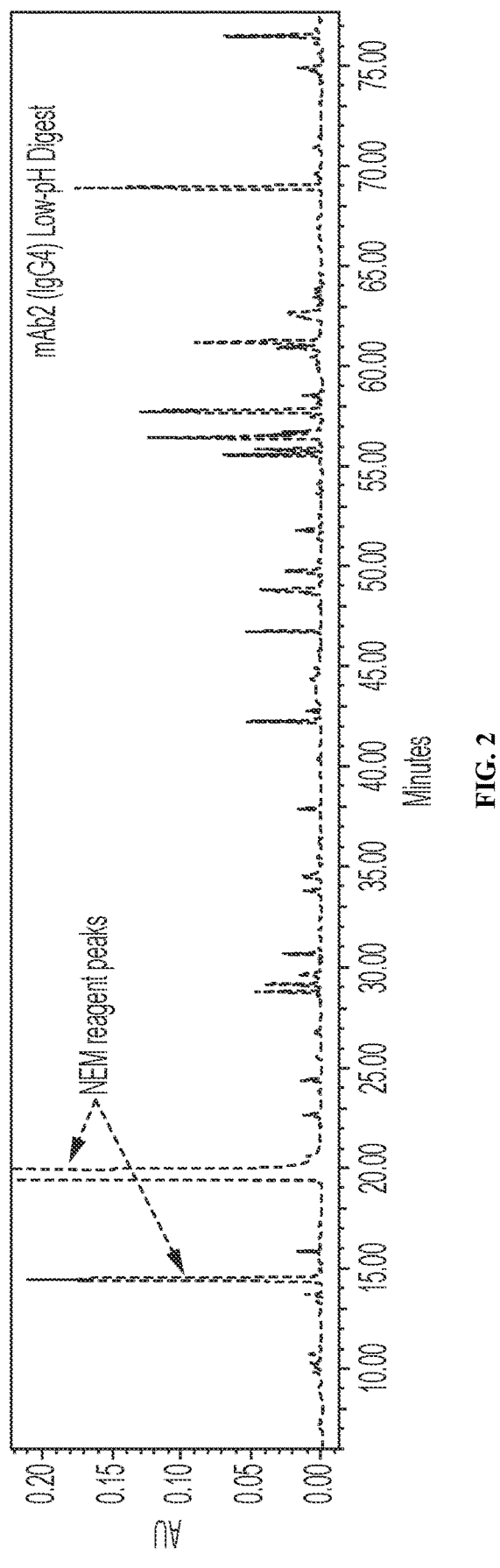
FIG. 2 shows a UV chromatogram of mAb 1 obtained from low pH non-reduced peptide mapping analysis of mAb2 prepared in low pH non-reducing peptide mapping conditions according to an exemplary embodiment.

The UV chromatograms of the peptide mapping analysis of mAb1 is shown in FIG. 1. Two UV peaks of NEM appear at around 15 minutes and 20 minutes. These UV peaks appear to interfere with the peptide peak reporting window of mAb 1. Similarly, for mAb2 the NEM peaks appear to interfere with its peptide peak reporting window (FIG. 2).

It is well known that acidic pH can effectively prevent disulfide scrambling during sample preparation (Wang et al., 2016, *Anal Biochem*, 495:21-8; Liu et al., 2014, *Mol Cell Proteomics*, 13(10):2776-86; Sung et al., 2016, *Biochim Biophys Acta*, 1864(9):1188-1194). As shown in FIG. 1, the most abundant disulfide scrambled peptides were not observed in the low pH condition. However, mAb 1 reporting window includes a peak for the HC-LC disulfide (see FIG. 3, SEQ ID. NO.: 1) with UV reportable peak at around 5 minutes. This requires that the protein characterization include a wider UV reporting window from around 5 minutes.

Figure 3:
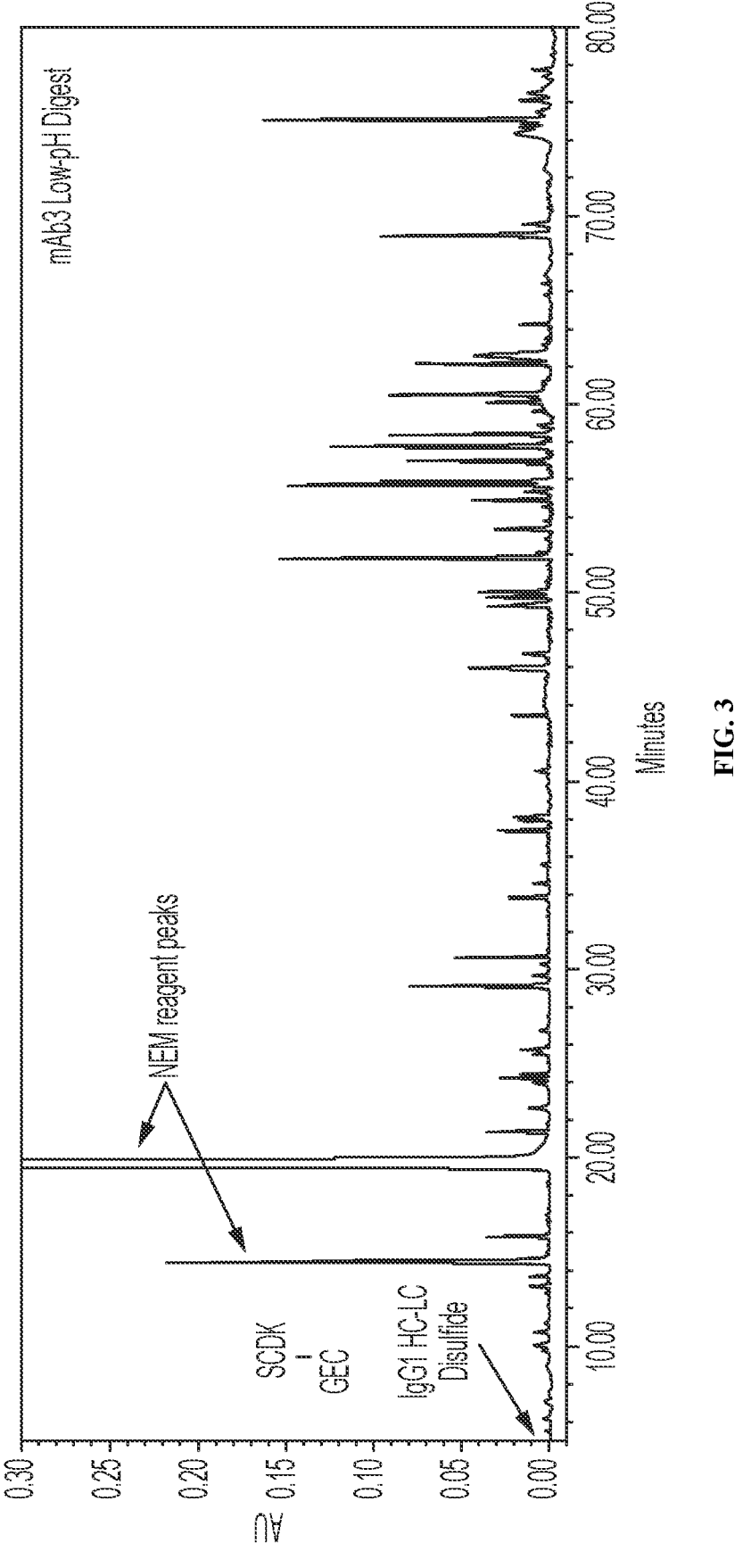
FIG. 3 shows a UV chromatogram of mAb 1 obtained from low pH non-reduced peptide mapping analysis of mAb1 prepared in low pH non-reducing peptide mapping conditions identifying an IgG1 disulfide according to an exemplary embodiment. Figure discloses SEQ ID NO: 13.

A complication from the low pH digestion method is that although the acidic pH method can effectively prevent disulfide scrambling during sample preparation, intense interference peaks at a retention times of 15 minutes and 20 minutes dominates the UV chromatograms, as shown in FIG. 3. NEM generates stereoisomers for each alkylated cysteine (4), and as a result, NEM-alkylated peptides produce double peaks in LC/MS and UV HPLC. This peak is due to N-Ethylmaleimide (NEM) alkylation reagent peak. In addition to its negative impact on the quality of UV chromatograms, this intense reagent peak could mask other tryptic peptide peaks from mAb digestion. Also, since NEM will form such dominant peaks in the early part of the RP-HPLC gradient, it may interfere with analysis of hydrophilic peptides.

Additionally, since acidic pH is not ideal for most commonly used enzymes, potentially decreased digestion efficiency of the low pH method could compromise method reproducibility and precision, even when two digestive enzymes are used. Increased numbers of mis-cleaved sites in acidic pH conditions add extraneous features to chromatograms and muddle assignment of disulfide peptides. All of these adverse factors negatively impact the low pH method for UV-based peptide mapping method qualification. Therefore, a need exists for a method that can restrict disulfide scrambling during sample preparation at basic pH conditions

Example 2. NEM-Like Alkylation Agents for Non-Reducing Peptide Mapping Method NEM is used widely in the industry as an alkylating agent. It performs fast and complete alkylation due to high reactivity of strained ring structure. Further, any protocol-induced disulfide scrambling is almost completely blocked at acidic pH. The NEM dominant peak with a retention time of 20 minute and a strong UV signal however, poses a concern since it interferes with the chromatogram, as seen for mAb 1 and mAb2 in Example 1 above.

The 20 minute retention time can be theoretically reduced by reducing the hydrophobicity of NEM while maintaining its high reactivity and stability as an alkylating agent during sample preparation at low pH.

Figure 4:
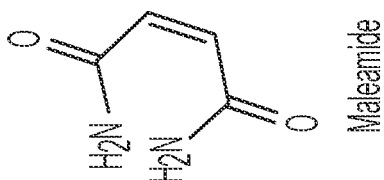
FIG. 4 shows structures of NEM analogs, maleimide, N-hydroxy maleimide and maleamide according to an exemplary embodiment.
Figure 4:
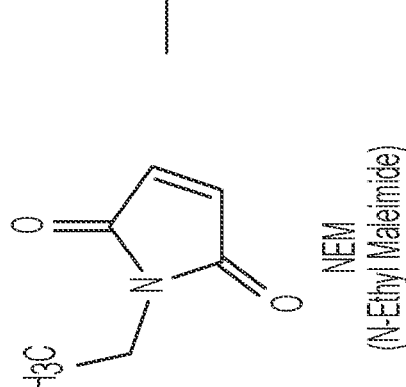

Protein characterization of mAb1 was carried out using the low pH digestion protocol as published by Promega's AccuMAP low pH digestion product. But this protocol was modified to replace NEM with (a) maleimide, (b) maleamide, and (c) N-hydroxy maleimide (Structures of which are shown in FIG. 4). All these analogs are more hydrophilic than NEM.

Figure 5:
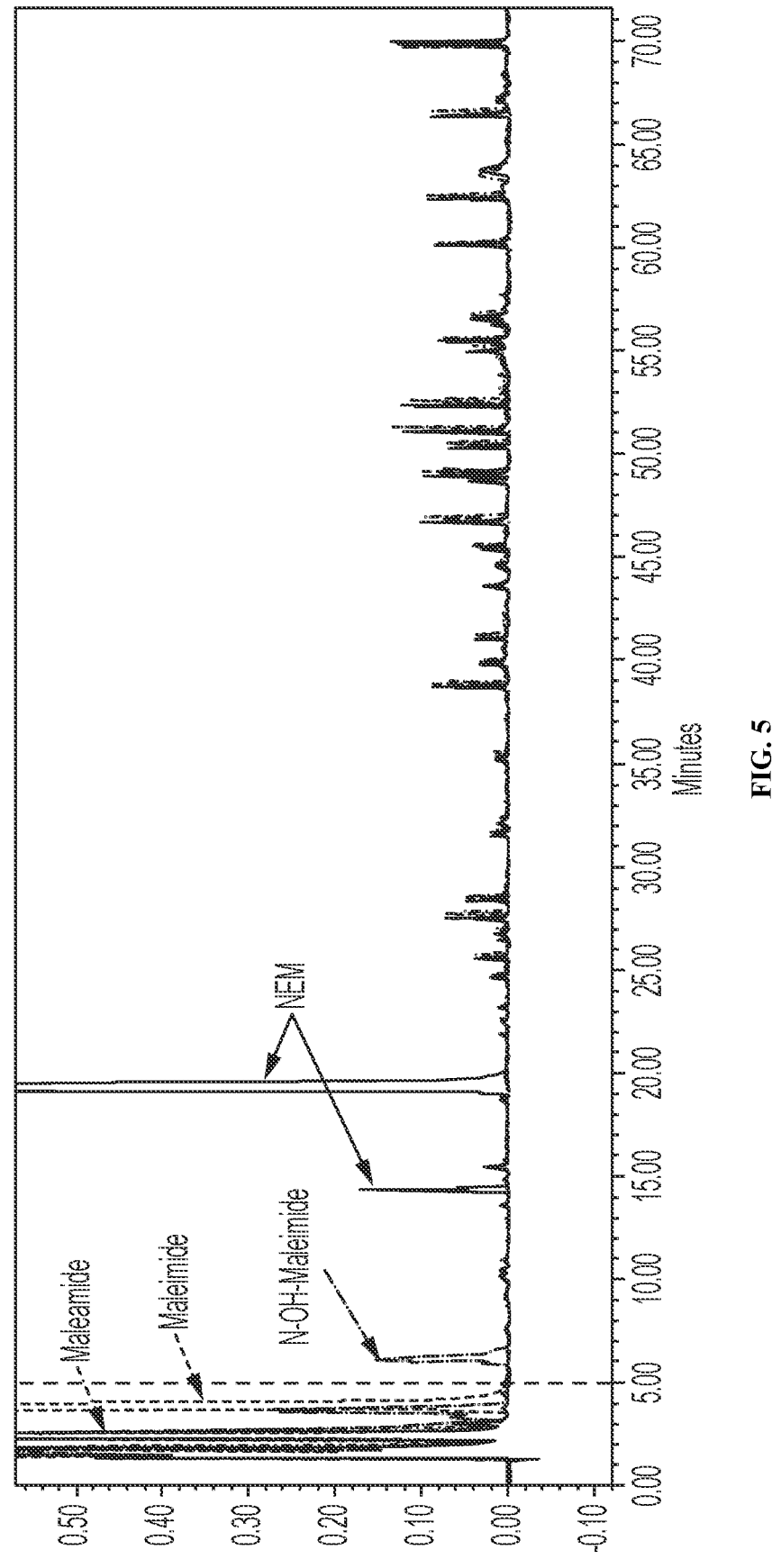
FIG. 5 shows UV chromatograms of low pH non-reduced peptide mapping analysis of mAb 1 using NEM, maleimide, N-hydroxy maleimide and maleamide according to an exemplary embodiment.

The UV chromatograms of the peptide mapping analysis of mAb1 using (a) maleimide, (b) maleamide, and (c) N-hydroxy maleimide is shown in FIG. 5 as overlapped on UV chromatograms of the peptide mapping analysis of mAb1 using NEM. Among the UV peaks for (a) maleimide, (b) maleamide, and (c) N-hydroxy maleimide, the UV peaks for maleimide and maleamide appear prior to the retention time of 5 minutes. Thus, these peaks might not pose any interference with the peptide peak reporting window of mAb 1 and generally most proteins.

Example 3. Prevention of Disulfide Scrambling by NEM Alternatives

Protein characterization of mAb3 (IgG4 antibody) was carried out using the low pH digestion protocol as published by low pH non-reduced digestion method. In addition, the protocol was repeated by replacing NEM with (a) maleimide, (b) maleamide, and (c) N-hydroxy maleimide.

The AccuMAP low pH protein digestion kit from Promega was used for low pH non-reduced peptide mapping sample preparation. The protocol followed the manufacturer's technical manual with minor modifications. Briefly, samples (100 μg) were diluted to about 5 μg/μL using 8 M guanidine hydrochloride, pH about 5.6 solution. The diluted samples were alkylated in 8 mM N-Ethylmaleimide (NEM) and incubated at 50° C. for 30 minutes at a pH of 5.7. The alkylated samples were pre-digested at 37° C. for 1 hour using low pH resistant rLys-C from the kit. Then, the samples were diluted five-fold with low pH reaction buffer and digested another 3 hours by adding modified trypsin and low pH resistant rLys-C following the ratio of enzyme: substrate specified by the manufacturer. Digestion was quenched by adding TFA to a final concentration of 0.3% before LC-MS analysis.

To test the degree to which addition of (a) maleimide, (b) maleamide, and (c) N-hydroxy maleimide prevents disulfide scrambling, the two disulfide scrambled peptides were evaluated for mAb3: STSESTAALGCLVK (SEQ ID NO.: 2) and TYTCNVDHKPSNTK (DEQ ID NO.: 3).

Figure 6C:
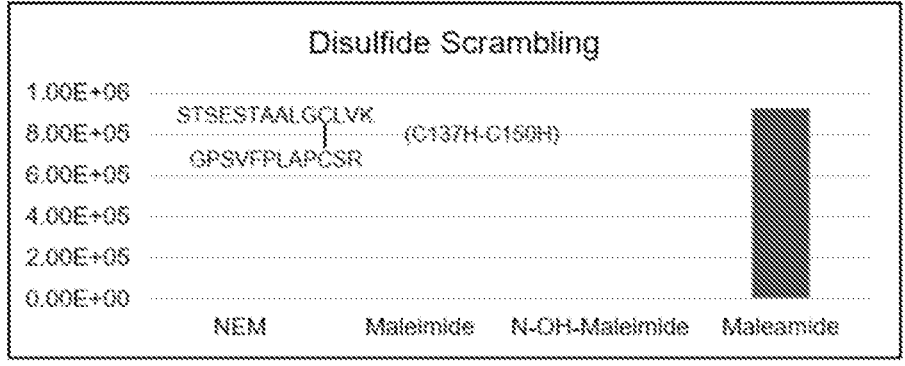
FIG. 6C shows a normalized peak area of a disulfide scrambling of disulfide (C137H—C150H) from low pH non-reduced peptide mapping analysis of mAb3 using NEM, maleimide, N-hydroxy maleimide and maleamide according to an exemplary embodiment. Figure discloses SEQ ID NOS 4-5, respectively, in order of appearance.

As shown in FIGS. 6A and 6B, the best results were obtained on using NEM, maleimide and N-hydroxy maleimide, where the peak areas of the two peptides as alkylated free thiols were significant compared to the non-alkylated free thiols (FIG. 6B). Lastly, the scrambled peptides were reduced significantly to negligible levels by NEM, maleimide and N-hydroxy maleimide. Thus, use of maleimide and N-hydroxy maleimide instead of NEM can prevent disulfide scrambling of the disulfide (C137H—C150H) comparably (see FIG. 6C). However, maleamide reacted slowly and did not produce similar alkylation profile as maleimide and N-hydroxy maleimide (FIGS. 6A-6C).

Figure 7:
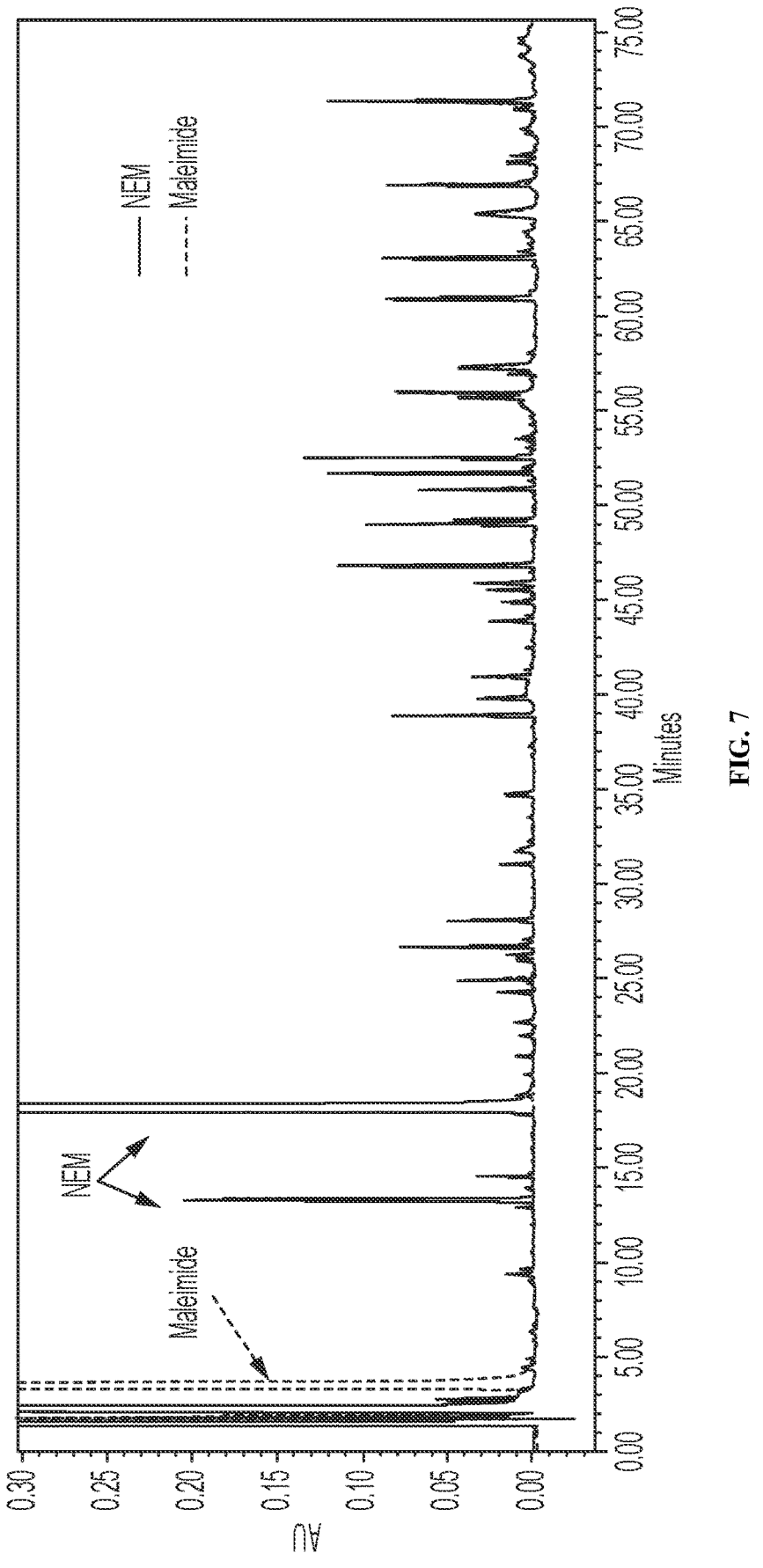
FIG. 7 shows UV chromatograms of low pH non-reduced peptide mapping analysis of mAb3 using NEM and maleimide according to an exemplary embodiment.

Maleimide provided a valuable alternative to NEM since it was found to be as reactive as NEM with complete blocking of scrambled disulfide peptides. The digestion profile by NEM and maleimide are comparable. The only significant difference between them is due to the reagent peaks (FIG. 7). It also had a retention time of 4 minutes (150 mm C18 column), and thus is clear of UV peptide reporting window (5-80 minutes). Lastly, it also provides an inexpensive alternative to be used for routine protein characterization.

Example 4. The Effect of Different Concentrations of Maleimide on the Non-Reducing Peptide Mapping Digestion Method Protein characterization of mAb3 (IgG4 antibody)) was further carried out as per the low pH digestion protocol as described in Example 3 using no alkylating agent (control), 1 mM maleimide, 2 mM maleimide, and 4 mM maleimide.

Figure 8A:
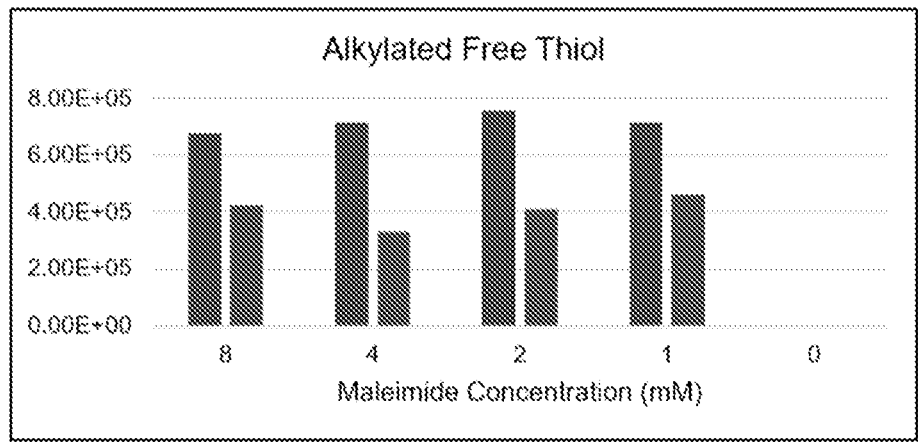
FIG. 8A shows a normalized peak area of alkylated free thiols (STSESTAALGCLVK (SEQ ID NO.: 2) and TYTCNVDHKPSNTK (SEQ ID NO.: 3)) from non-reduced peptide mapping analysis of mAb3 using a control, 1 mM maleimide, 2 mM maleimide, 4 mM maleimide, and 8 mM maleimide, according to an exemplary embodiment.
Figure 8B:
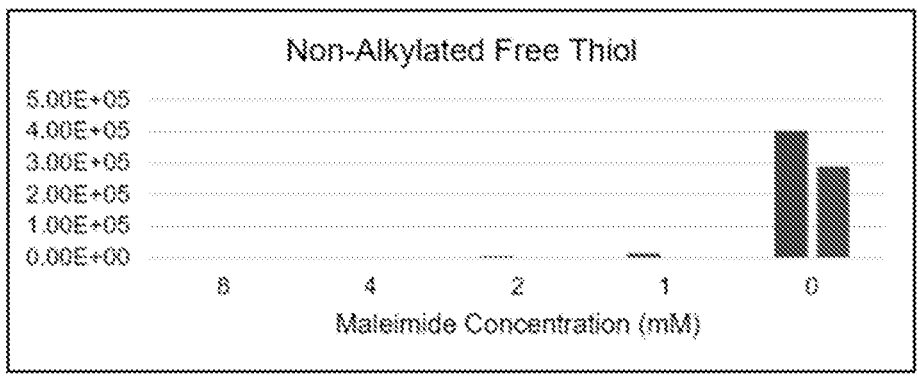
FIG. 8B shows a normalized peak area of non-alkylated free thiols (STSESTAALGCLVK (SEQ ID NO.: 2) and TYTCNVDHKPSNTK (SEQ ID NO.: 3)) from non-reduced peptide mapping analysis of mAb3 using a control, 1 mM maleimide, 2 mM maleimide, 4 mM maleimide, and 8 mM maleimide, according to an exemplary embodiment
Figure 8C:
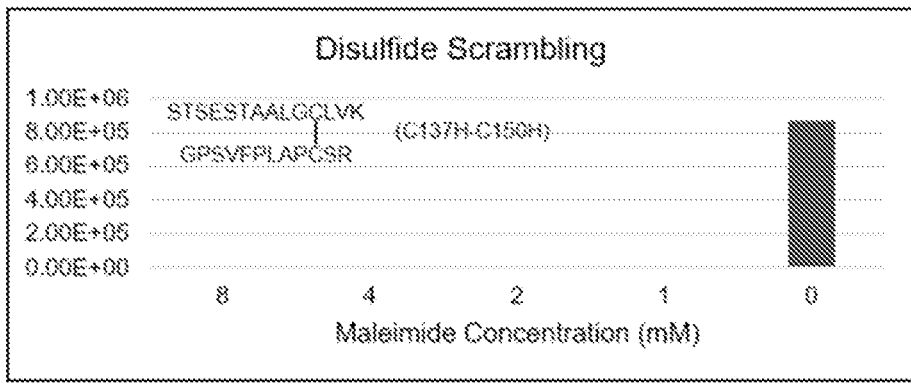
FIG. 8C shows a normalized peak area of a disulfide scrambling of disulfide (C137H—C150H) from non-reduced peptide mapping analysis of mAb3 using a control, 1 mM maleimide, 2 mM maleimide, 4 mM maleimide, and 8 mM maleimide, according to an exemplary embodiment. Figure discloses SEQ ID NOS 4-5, respectively, in order of appearance.

To test the degree to which concentration of maleimide can prevent disulfide scrambling, the two disulfide scrambled peptides were evaluated for mAb3: STSES-TAALGCLVK (SEQ ID NO.: 2) and TYTCNVDHKPSNTK (DEQ ID NO.: 3). As shown in FIGS. 8A and 8B, the best results were obtained on using 4 mM and 8 mM maleimide, where the peak areas of the two peptides as alkylated free thiols (FIG. 7A) were significant compared to the non-alkylated free thiols (FIG. 8B). Use of >1 mM maleimide provided almost 99% alkylation efficiency. Lastly, the scrambled peptides were reduced to negligible levels by using 2 mM, 4 mM and 8 mM maleimide. Thus, use of 4 mM maleimide or more can block disulfide scrambling of the disulfide (C137H—C150H) completely (see FIG. 7C). However, maleamide reacted slowly and did not produce similar alkylation profile as maleimide and N-hydroxy maleimide (FIGS. 8A-8C).

Example 5. Half-Acidic Digestion Method Using Maleimide

Figure 9:
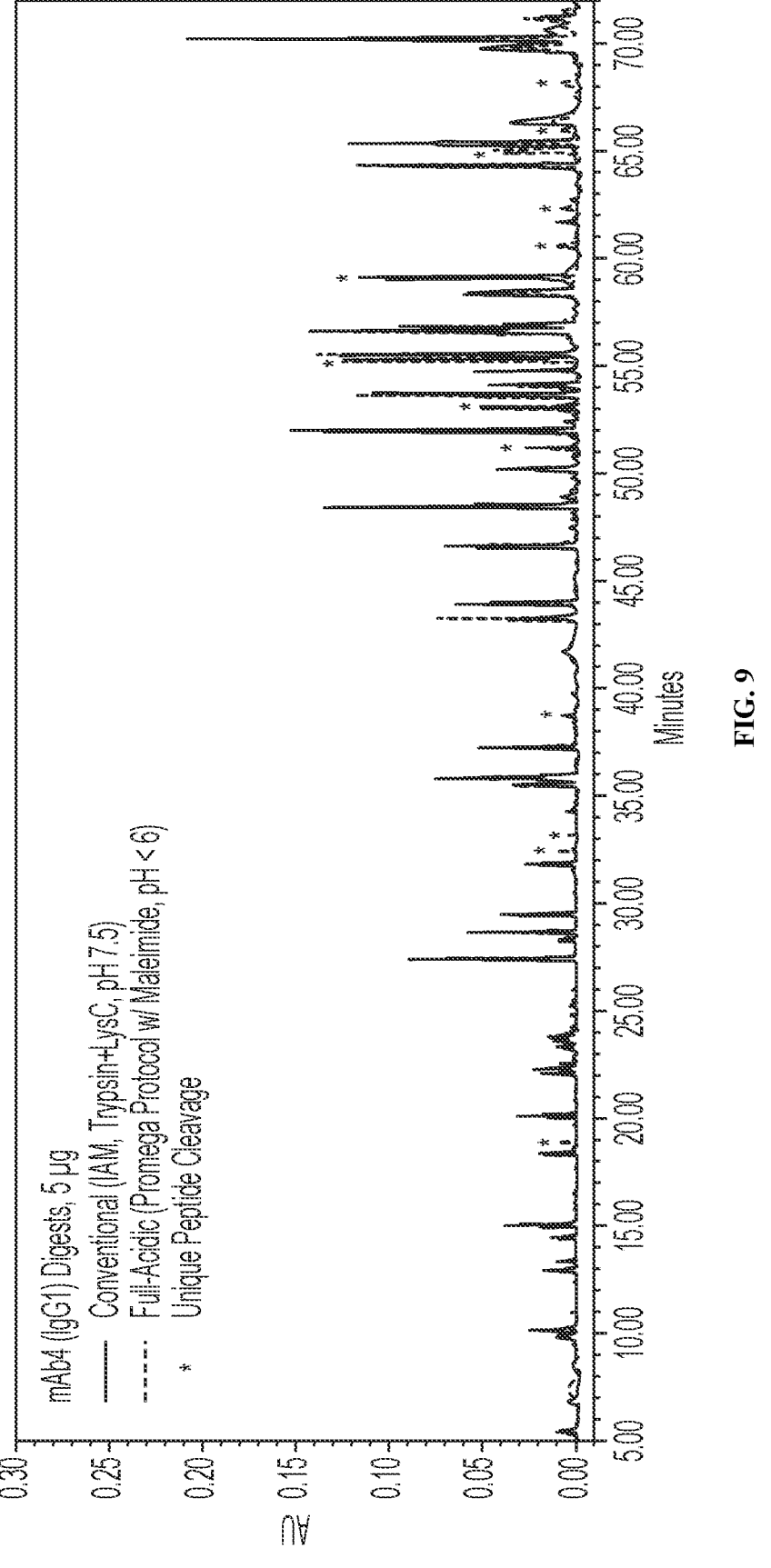
FIG. 9 shows UV chromatograms of low pH non-reduced peptide mapping analysis of mAb4 using maleimide and conventional non-reduced peptide mapping analysis of mAb4 according to an exemplary embodiment.

AccuMAP low pH protein digestion kit from Promega is based on the presumption that while "[c]ommon reducing and alkylating agents favor alkaline pH. Because alkaline pH induces deamidation and disulfide bond scrambling, [the modified procedure] is made to be compatible with low pH." However, this method can lead to a digest profile that does not identify unique peptide cleavages as seen in FIG. 9 (marked by an asterisk).

Protein characterization of mAb4 (IgG1 antibody) was carried out using the low pH digestion protocol as published by low pH non-reducing protein mapping digestion method using 8 mM maleimide as performed in Example 2. This was compared to a conventional digest (as per the regular non-reducing peptide mapping method) using iodoacetamide, which essentially caps all endogenous free thiols as well as artifact thiols before any scrambling can occur. This method is performed at a pH of 7.5.

Figure 10:
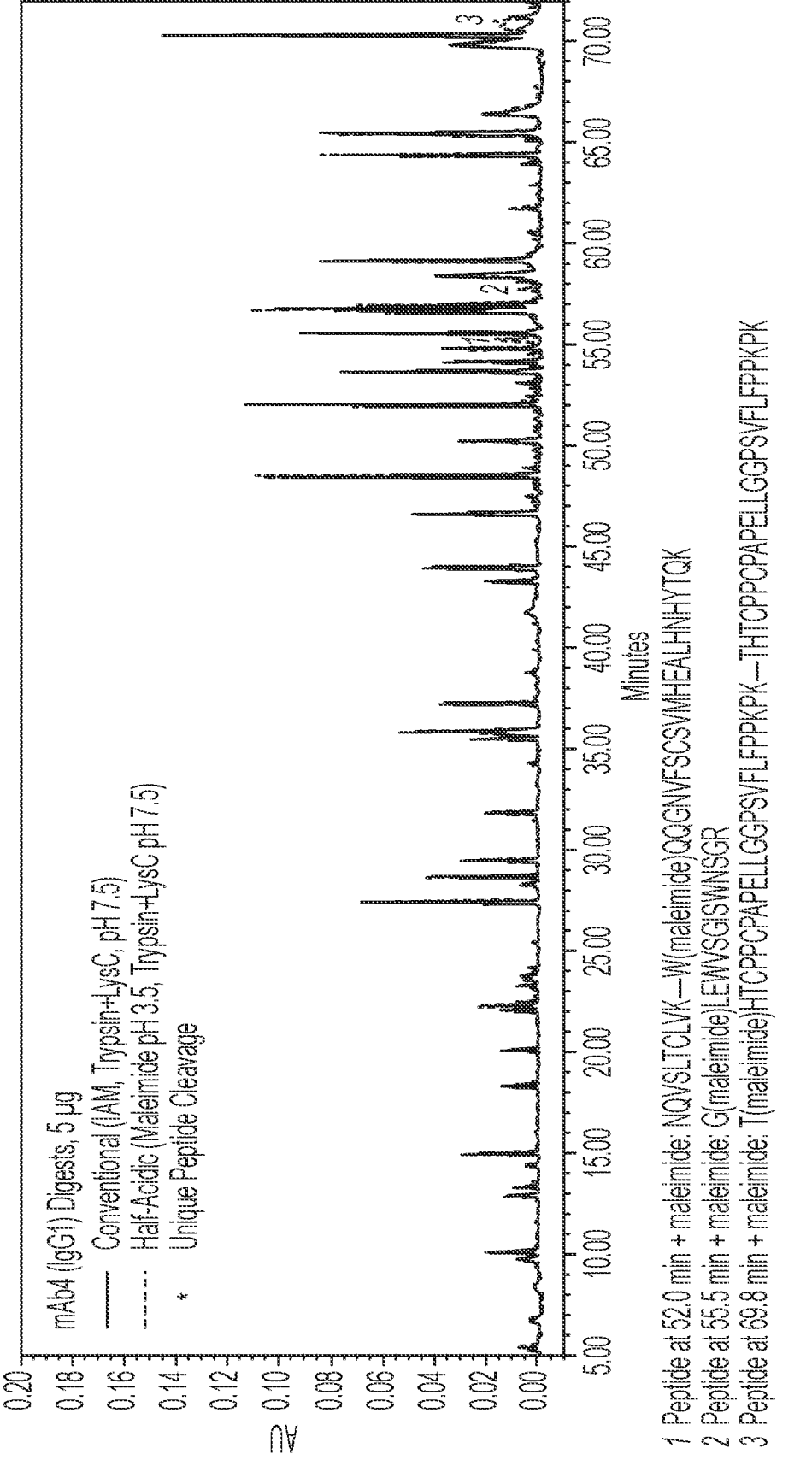
FIG. 10 shows UV chromatograms of 'half-acidic' non-reduced peptide mapping analysis of mAb4 using maleimide and conventional non-reduced peptide mapping analysis of mAb4 according to an exemplary embodiment. Figure discloses SEQ ID NOS 6-10, respectively, in order of appearance.

The non-reduced peptide mapping method using maleimide was modified to adapt the digestion protocol as used by the conventional method instead of using the Low pH Modified Trypsin and/or Low pH Resistant rLys-C at pH of 5.3, and the digestion was carried out at a pH of 7.5 using 1:20 E/S of trypsin, 1:50 E/S of rLysC. The peptide mapping obtained as a result of such a half-acidic protocol (alkylation at acidic condition and digestion at non-acidic condition) was comparable to the mapping by a conventional digest (as per the regular non-reducing peptide mapping method) (See FIG. 10). The half-acidic method is able to identify three distinct peptides which were not observed in conventional non-reducing peptide mapping method (See the peptides at 52 minutes, 55.5 minutes and 69.8 minutes).

Figure 11:
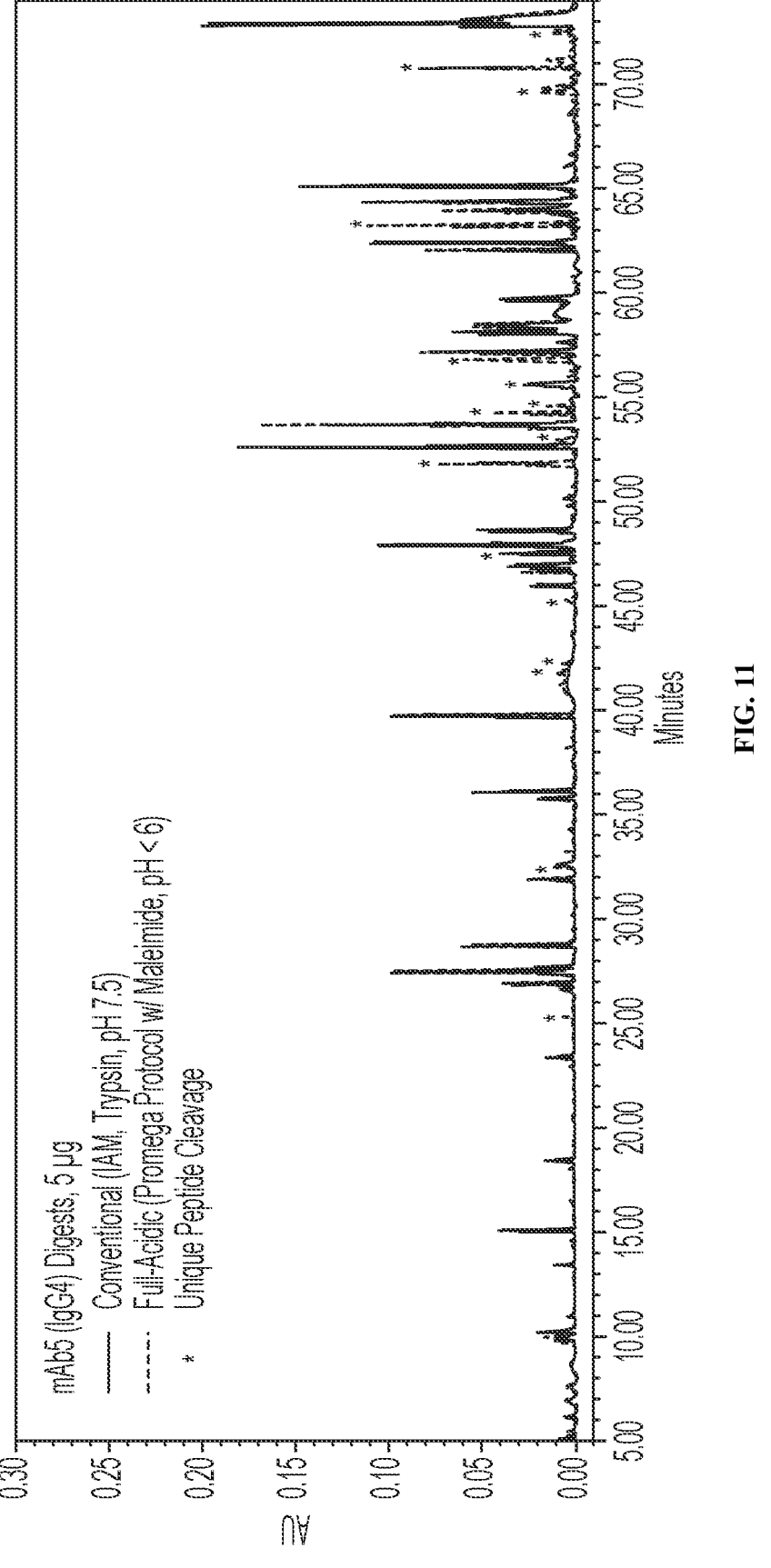
FIG. 11 shows UV chromatograms of low pH non-reduced peptide mapping analysis of mAb5 using maleimide and conventional non-reduced peptide mapping analysis of mAb4 according to an exemplary embodiment.

Example 6. Reproducibility of the Half-Acidic Digestion Method Using Maleimide The half-acidic digest and conventional digest profiles of an IgG4 antibody, mAb5 was evaluated. The protein characterization of mAb5 was carried out using the low pH digestion protocol as published by low pH non-reducing protein mapping digestion method using 8 mM maleimide as performed in Example 2. This was compared to a conventional digest (as per the regular non-reducing peptide mapping method) using only trypsin instead of Trypsin+LysC (at a pH of 7.5). As seen for mAb4, the digest profile obtained using the low pH non-reducing peptide mapping and conventional peptide mapping do not match (see FIG. 11, the unique peptides not identified by non-reducing peptide mapping are marked by an asterisk).

Figure 12:
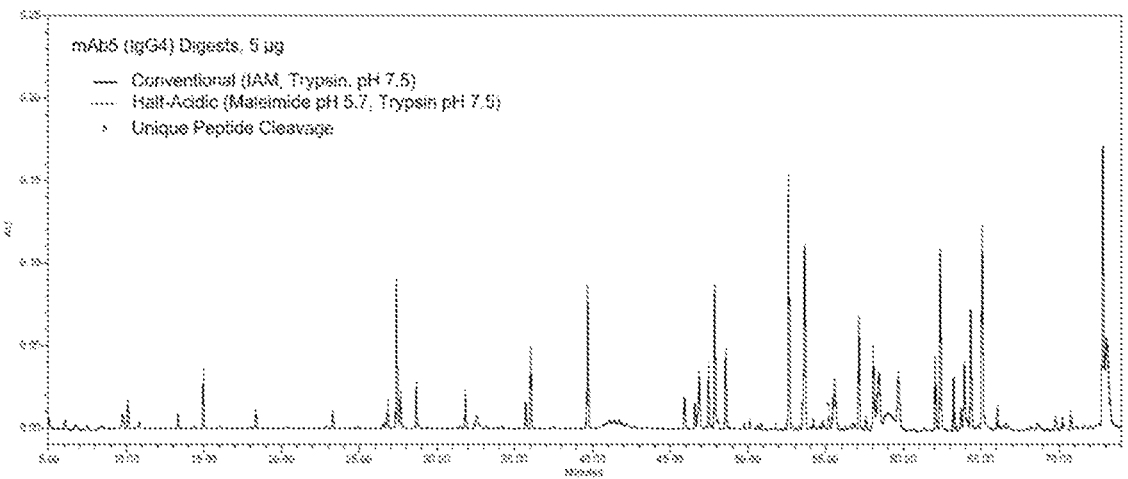
FIG. 12 shows UV chromatograms of 'half-acidic' non-reduced peptide mapping analysis of mAb5 using maleimide and conventional non-reduced peptide mapping analysis of mAb4 according to an exemplary embodiment. Figure discloses SEQ ID NOS 12 and 11, respectively, in order of appearance.

The non-reduced peptide mapping method using maleimide was modified to adapt the digestion protocol as used by the conventional method instead of using the Low pH Modified Trypsin and/or Low pH Resistant rLys-C at pH of 5.3, the digestion was carried out at a pH of 7.5 using 1:20 E/S Trypsin. The peptide mapping obtained as a result of such a half-acidic protocol was comparable to the mapping by a conventional digest (as per the regular non-reducing peptide mapping method) (See FIG. 12). The half-acidic method is able to identify a distinct peptide which was not observed in low pH non-reducing peptide mapping method (See the peptides at 52.6 minutes.

Figure 13:
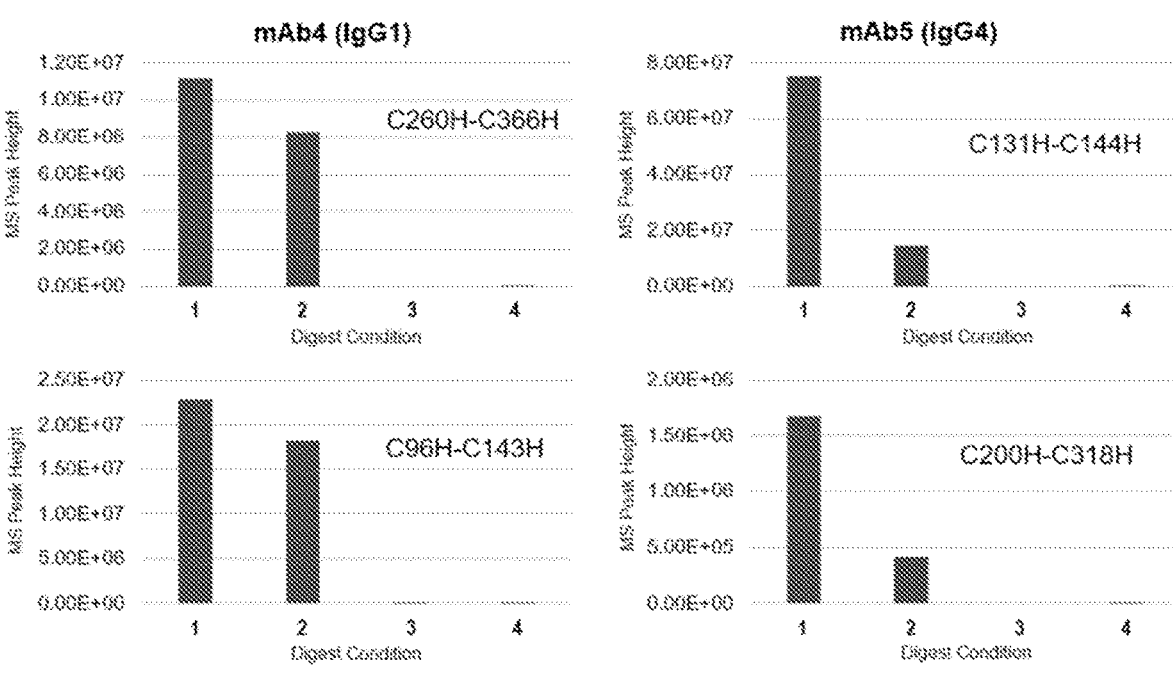
FIG. 13 shows the impact of digestion conditions on disulfide scrambling of peptides of mAb4 and mAb5, where the conditions are (1) no alkylation, basic digestion; (2) basic alkylation (IAM), basic digestion; (3) acidic alkylation (maleimide), acidic digestion; and (4) acidic alkylation (maleimide), basic digestion, according to exemplary embodiments.

Lastly, to compare the impact of digestion conditions on disulfide scrambling, results from the different digestion conditions were compared by comparing the normalized peak area of a disulfide scrambled peptide from mAb4 and from mAb5 obtained from each of the conditions. FIG. 13 shows that use of maleimide with acidic and basic digestions lead to negligible levels of disulfide scrambling.

The method developed herein offers several advantages over the commercial kits such as Promega's "Low-pH Digestion Kit," which uses proprietary buffers/reagents to perform digestions entirely under acidic conditions and was developed to minimize disulfide scrambling and some other PTMs, creates digestion peptide profiles with significant differences (non-specific cleavages) compared to traditional basic-pH digests. Such commercial kits are now rendered obsolete for non-reduced peptide mapping assays after the method development described herein.

---

SEQUENCE LISTING

Sequence total quantity: 13
SEQ ID NO: 1            moltype =    length =
SEQUENCE: 1
000

SEQ ID NO: 2            moltype = AA  length = 14
FEATURE                 Location/Qualifiers
source                  1..14
                        mol_type = protein
                        organism = synthetic construct
SEQUENCE: 2
STSESTAALG CLVK                                                       14

SEQ ID NO: 3            moltype = AA  length = 14
FEATURE                 Location/Qualifiers

```
source                  1..14
                        mol_type = protein
                        organism = synthetic construct
SEQUENCE: 3
TYTCNVDHKP SNTK                                                     14

SEQ ID NO: 4            moltype = AA  length = 14
FEATURE                 Location/Qualifiers
source                  1..14
                        mol_type = protein
                        organism = synthetic construct
DISULFID                11
                        note = interchain disulfide bond with the cysteine at
                         position 10 of SEQ ID NO: 5
SEQUENCE: 4
STSESTAALG CLVK                                                     14

SEQ ID NO: 5            moltype = AA  length = 12
FEATURE                 Location/Qualifiers
source                  1..12
                        mol_type = protein
                        organism = synthetic construct
DISULFID                10
                        note = interchain disulfide bond with the cysteine at
                         position 11 of SEQ ID NO: 4
SEQUENCE: 5
GPSVFPLAPC SR                                                       12

SEQ ID NO: 6            moltype = AA  length = 10
FEATURE                 Location/Qualifiers
source                  1..10
                        mol_type = protein
                        organism = synthetic construct
DISULFID                7
                        note = interchain disulfide bond with the cysteine at
                         position 9 of SEQ ID NO: 7
SEQUENCE: 6
NQVSLTCLVK                                                          10

SEQ ID NO: 7            moltype = AA  length = 23
FEATURE                 Location/Qualifiers
source                  1..23
                        mol_type = protein
                        organism = synthetic construct
SITE                    1
                        note = Maleimide modified residue
DISULFID                9
                        note = interchain disulfide bond with the cysteine at
                         position 7 of SEQ ID NO: 6
SEQUENCE: 7
WQQGNVFSCS VMHEALHNHY TQK                                           23

SEQ ID NO: 8            moltype = AA  length = 14
FEATURE                 Location/Qualifiers
source                  1..14
                        mol_type = protein
                        organism = synthetic construct
SITE                    1
                        note = Maleimide modified residue
SEQUENCE: 8
GLEWVSGISW NSGR                                                     14

SEQ ID NO: 9            moltype = AA  length = 26
FEATURE                 Location/Qualifiers
source                  1..26
                        mol_type = protein
                        organism = synthetic construct
SITE                    1
                        note = Maleimide modified residue
DISULFID                4
                        note = interchain disulfide bond with the cysteine at
                         position 4 of SEQ ID NO: 10
DISULFID                7
                        note = interchain disulfide bond with the cysteine at
                         position 7 of SEQ ID NO: 10
SEQUENCE: 9
THTCPPCPAP ELLGGPSVFL FPPKPK                                        26

SEQ ID NO: 10           moltype = AA  length = 26
```

-continued

```
FEATURE              Location/Qualifiers
source               1..26
                     mol_type = protein
                     organism = synthetic construct
DISULFID             4
                     note = interchain disulfide bond with the cysteine at
                      position 4 of SEQ ID NO: 9
DISULFID             7
                     note = interchain disulfide bond with the cysteine at
                      position 7 of SEQ ID NO: 9
SEQUENCE: 10
THTCPPCPAP ELLGGPSVFL FPPKPK                                    26

SEQ ID NO: 11        moltype = AA  length = 23
FEATURE              Location/Qualifiers
source               1..23
                     mol_type = protein
                     organism = synthetic construct
SITE                 1
                     note = Maleimide modified residue
DISULFID             9
                     note = interchain disulfide bond with the cysteine at
                      position 7 of SEQ ID NO: 12
SEQUENCE: 11
WQEGNVFSCS VMHEALHNHY TQK                                       23

SEQ ID NO: 12        moltype = AA  length = 10
FEATURE              Location/Qualifiers
source               1..10
                     mol_type = protein
                     organism = synthetic construct
DISULFID             7
                     note = interchain disulfide bond with the cysteine at
                      position 9 of SEQ ID NO: 11
SEQUENCE: 12
NQVSLTCLVK                                                      10

SEQ ID NO: 13        moltype = AA  length = 4
FEATURE              Location/Qualifiers
source               1..4
                     mol_type = protein
                     organism = synthetic construct
DISULFID             2
                     note = interchain disulfide bond
SEQUENCE: 13
SCDK                                                            4
```

What is claimed is:

1. A method for performing a non-reduced peptide mapping of a protein of interest in a sample, said method comprising:
   a. contacting said sample to a NEM analog to form an alkylated protein of interest, wherein the NEM analog is maleimide or N-hydroxy maleimide;
   b. contacting said alkylated protein of interest to at least one digestive enzyme to form a peptide digest; and
   c. analyzing said peptide digest using liquid chromatography-mass spectrometry to obtain said non-reduced peptide mapping of said protein of interest.

2. The method of claim 1, wherein the NEM analog is maleimide.

3. The method of claim 1, wherein the concentration of NEM analog used to contact said sample is about 1 mM to about 10 mM.

4. The method of claim 1, wherein the concentration of NEM analog used to contact said sample is about 2 mM to about 8 mM.

5. The method of claim 1, wherein the concentration of NEM analog used to contact said sample is about 4 mM.

6. The method of claim 1, wherein said NEM analog is contacted with said sample at 50° C. for 30 minutes.

7. The method of claim 1, wherein said protein of interest is an antibody.

8. The method of claim 1, further comprising contacting said sample to at least one denaturation agent.

9. The method of claim 1, wherein said at least one digestive enzyme is trypsin.

10. The method of claim 1, wherein said at least one digestive enzyme is Lys-C.

11. The method of claim 1, wherein said at least one digestive enzyme is Lys-C and trypsin.

12. The method of claim 1, wherein said digestion is conducted at a pH of about 7 to about 8.

13. The method of claim 1, wherein said digestion is conducted at a pH of about 7 to about 7.5.

14. The method of claim 1, wherein said digestion is conducted at a pH of about 5 to about 6.

15. The method of claim 1, wherein said digestion is conducted at a pH of about 5.3 to about 7.

16. A method for characterizing a protein of interest in a sample, said method comprising:
   a. contacting said sample to a NEM analog to form an alkylated protein of interest, wherein the NEM analog is maleimide or N-hydroxy maleimide;
   b. contacting said alkylated protein of interest to at least one digestive enzyme to form a peptide digest; and
   c. analyzing said peptide digest using liquid chromatography-mass spectrometry to obtain a non-reduced peptide mapping to characterize said protein of interest.

17. The method of claim 16, wherein the NEM analog is maleimide.

18. The method of claim 17, wherein the concentration of maleimide used to contact said sample is about 2 mM to about 8 mM.

19. The method of claim 18, wherein the concentration of maleimide used to contact said sample is about 4 mM.

20. The method of claim 16, further comprising contacting said sample to at least one denaturation agent.

\* \* \* \* \*